US009603943B2

(12) United States Patent
Kleiner et al.

(10) Patent No.: US 9,603,943 B2
(45) Date of Patent: *Mar. 28, 2017

(54) POLYESTERAMIDE PLATFORM FOR SITE SPECIFIC DRUG DELIVERY

(71) Applicant: Abbott Cardiovascular Systems Inc., Santa Clara, CA (US)

(72) Inventors: Lothar W. Kleiner, Los Altos, CA (US); Syed Hossainy, Hayward, CA (US); Stephen Pacetti, San Jose, CA (US); Jessica DesNoyer, Bedford, MA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/750,732

(22) Filed: Jun. 25, 2015

(65) Prior Publication Data

US 2015/0290336 A1    Oct. 15, 2015

Related U.S. Application Data

(60) Continuation of application No. 14/493,197, filed on Sep. 22, 2014, now Pat. No. 9,095,619, which is a division of application No. 14/149,533, filed on Jan. 7, 2014, now Pat. No. 8,865,148, which is a division of application No. 11/405,976, filed on Apr. 17, 2006, now Pat. No. 8,658,210.

(51) Int. Cl.

| | | |
|---|---|---|
| *A61K 31/74* | (2006.01) | |
| *A61K 47/48* | (2006.01) | |
| *A61K 9/00* | (2006.01) | |
| *A61K 9/08* | (2006.01) | |
| *A61K 9/10* | (2006.01) | |
| *A61K 31/337* | (2006.01) | |
| *A61K 31/4745* | (2006.01) | |
| *A61K 47/34* | (2017.01) | |
| *C08L 77/12* | (2006.01) | |
| *A61K 31/727* | (2006.01) | |

(52) U.S. Cl.
CPC ...... *A61K 47/48207* (2013.01); *A61K 9/0024* (2013.01); *A61K 9/08* (2013.01); *A61K 9/10* (2013.01); *A61K 31/337* (2013.01); *A61K 31/4745* (2013.01); *A61K 31/727* (2013.01); *A61K 47/34* (2013.01); *A61K 47/482* (2013.01); *A61K 47/48215* (2013.01); *C08L 77/12* (2013.01); *C08L 2205/02* (2013.01)

(58) Field of Classification Search
CPC .............................................. A61K 47/48207
See application file for complete search history.

(56) References Cited

U.S. PATENT DOCUMENTS

| | | |
|---|---|---|
| 5,324,519 A | 6/1994 | Dunn et al. |
| 5,684,889 A | 11/1997 | Chen et al. |
| 5,759,563 A | 6/1998 | Yewey et al. |
| 5,919,893 A | 7/1999 | Roby et al. |
| 6,692,466 B1 | 2/2004 | Chow et al. |
| 6,703,040 B2 | 3/2004 | Katsarava et al. |
| 7,273,469 B1 | 9/2007 | Chan et al. |
| 2003/0032938 A1 | 2/2003 | Altman |
| 2004/0009229 A1 | 1/2004 | Unger et al. |
| 2004/0170685 A1* | 9/2004 | Carpenter et al. . A61K 31/7048 424/468 |
| 2005/0131201 A1 | 6/2005 | Pacetti et al. |
| 2005/0201972 A1 | 9/2005 | Seo et al. |
| 2005/0208091 A1 | 9/2005 | Pacetti |
| 2005/0265960 A1 | 12/2005 | Pacetti et al. |
| 2006/0034889 A1 | 2/2006 | Jo et al. |
| 2006/0074191 A1 | 4/2006 | DesNoyer et al. |
| 2006/0177416 A1 | 8/2006 | Turnell et al. |
| 2006/0286063 A1 | 12/2006 | Shebuski et al. |
| 2012/0328706 A1 | 12/2012 | Turnell et al. |
| 2014/0105957 A1 | 4/2014 | Franken et al. |
| 2014/0120170 A1 | 5/2014 | Mihov et al. |
| 2014/0179802 A1 | 6/2014 | Franken et al. |
| 2014/0220099 A1 | 8/2014 | Draaisma et al. |

FOREIGN PATENT DOCUMENTS

| | | |
|---|---|---|
| JP | 5305135 | 11/1993 |
| JP | 2005533081 | 11/2005 |

(Continued)

OTHER PUBLICATIONS

Abbott Cardiovascular Systems, Non-final Office Action mailed Feb. 3, 2014 for U.S. Appl. No. 14/149,533.
Abbott Cardiovascular Systems, Final Office Action mailed Mar. 2, 2015, U.S. Appl. No. 14/493,197.
Abbott Cardiovascular Systems, Non-Final Office Action mailed Nov. 18, 2014 for U.S. Appl. No. 14/493,197.
Abbott Cardiovascular Systems, European Office Action mailed Nov. 11, 2014 for EP 07 755 524.1, 4 pages.
Abbott Cardiovascular Systems, International Search Report and Written Opinion dated Jan. 29, 2008 for PCT/US2007/009290.
Abbott Cardiovascular Systems, Non final office action dated Mar. 6, 2009 for U.S. Appl. No. 11/405,976.

(Continued)

*Primary Examiner* — Paul Dickinson
(74) *Attorney, Agent, or Firm* — Blakely Sokoloff Taylor & Zafman LLP

(57) ABSTRACT

A therapeutic agent delivery system formed of a specific type of poly(ester amide) (PEA), a therapeutic agent, and a water miscible solvent is described herein. A method of delivering the therapeutic agent delivery system by delivering the therapeutic agent delivery system formed of a PEA polymer, a therapeutic agent, and a water miscible solvent to a physiological environment and separating the phase of the therapeutic agent delivery system to form a membrane from the polymer to contain the therapeutic agent within the physiological environment is also described. Additionally disclosed is a kit including a syringe and a therapeutic agent delivery system within the syringe.

26 Claims, No Drawings

(56) References Cited

FOREIGN PATENT DOCUMENTS

| JP | 2008530206 | 8/2008 |
|---|---|---|
| WO | WO-0218477 A2 | 3/2002 |
| WO | WO-0218477 A3 | 3/2002 |
| WO | WO-0249573 A2 | 6/2002 |
| WO | WO-2004000269 | 12/2003 |
| WO | WO-2005020933 | 3/2005 |
| WO | WO-2005061024 A1 | 7/2005 |
| WO | WO-2005089824 A2 | 9/2005 |
| WO | WO-2005120453 | 12/2005 |
| WO | WO-2006058122 | 6/2006 |
| WO | WO-2006088647 A1 | 8/2006 |

OTHER PUBLICATIONS

Abbott Cardiovascular Systems, Final Office Action dated Aug. 27, 2009 for U.S. Appl. No. 11/405,976.
Abbott Cardiovascular Systems, Non final office action dated Feb. 19, 2010 for U.S. Appl. No. 11/405,976.
Abbott Cardiovascular Systems, International search report and written opinion dated Apr. 23, 2008 for PCT/US2007/018599.
Abbott Cardiovascular Systems, International Preliminary Report on Patentability dated Mar. 12, 2009 for PCT/US2007/018599.
Abbott Cardiovascular Systems, Non final office action dated Jul. 6, 2010 for U.S. Appl. No. 11/468,721.
Abbott Cardiovascular Systems, Final Office Action mailed Jul. 23, 2010 for U.S. Appl. No. 11/405,976.
Abbott Cardiovascular Systems, Final Office Action mailed Jan. 14, 2011 for U.S. Appl. No. 11/468,721.
Abbott Cardiovascular Systems, Japanese Office Action mailed Sep. 25, 2012, Japanese Appln. No. 2009-506531.
Abbott Cardiovascular Systems, European Office Action mailed May 11, 2009, European Appln. No. 07755524.1.
Abbott Cardiovascular Systems, European Office Action mailed Jan. 9, 2013, European Appln. No. 07755524.1.
Abbott Cardiovascular Systems, Japanese Notice of the Reasons for Refusal dated Jul. 30, 2013 for JP 2009-506531.
Armitage, Frances E., et al., "Polymeric Contrast Agents for Magnetic Resonance Imaging: Synthesis and Characterization of Gadolinium Diethylenetriaminepentaacetic Acid Conjugated to Polysaccharides", *Bioconjugate Chemistry*, vol. 1, No. 6, (Nov./Dec. 1990), 365-374.
DSM Biomedical, "DSM and Svelte Medical Systems Execute License and Supply Agreement for DSM's Proprietary Amino Acid-Based Drug Carrier for Svelte's new All-in-One Drug-Eluting Stent System", retrieved via Internet: www.medicaldevice-network.com/contractors/biotechnology/dsm1/presssvelte-license-amino-acid-stent.html, (Nov. 7, 2011), 2 pages.
Guo, Kai, et al., "Synthesis and Characterization of Novel Biodegradable Unsaturated Poly(ester amide)s", *Journal of Polymer Science: Part A: Polymer Chemistry*, vol. 43, (2005), 1463-1477.
Konan-Kouakou, Y. N., et al., "In vitro and in vivo activities of verteporfin-loaded nanoparticles", *Journal of Controlled Release*, vol. 103, (2005), 83-91.
Leonard, Shana, "Drug Delivery Technologies Show Some Backbone", *MPMN*, vol. 27, No. 8, retrieved via Internet: www.qmed.com/mpmn/article/drug-delivery-technologies-show-some-backbone, (Oct. 2011), 3 pages.
Roumeliotis, Gregory, "SurModics obtains new biodegradable polymers", retrieved via Internet: www.in-pharmatechnologist.com/Ingredients/SurModics-obtains-new-biodegradable-polymers, (May 15, 2006), 3 pages.
Teixeira, M., et al., "Development and characterization of PLGA nanosphere and nanocapsules containing xanthone and 3-methoxyxanthone", *European Journal of Pharmaceutics and Biopharmaceutics*, vol. 59, (2005), 491-500.
Thies, J., et al., "Slow-release latanoprost delivery by DSM's injectable PEA microfibers", DSM technical poster, (2014), 1 page.
Win, K. Y., et al., "Effects of particle size and surface coating on cellular uptake of polymeric nanoparticles for oral delivery of anticancer drugs", *Biomaterials*, vol. 26, (2005), 2713-2722.
Abbott Cardiovascular Systems, Examination report, EP App No. 07755524.1, (Jan. 22, 2016).
Abbott Cardiovascular Systems, Non-final Office Action, U.S. Appl. No. 14/590,590, (Apr. 15, 2016).

* cited by examiner

POLYESTERAMIDE PLATFORM FOR SITE SPECIFIC DRUG DELIVERY

CROSS-REFERENCE TO RELATED APPLICATION

This application is a continuation of co-pending U.S. patent application Ser. No. 14/493,197, filed Sep. 22, 2014, which application is a divisional of U.S. patent application Ser. No. 14/149,533, filed Jan. 7, 2014, now U.S. Pat. No. 8,865,148, which application is a divisional of U.S. patent application Ser. No. 11/405,976, filed Apr. 17, 2006, now U.S. Pat. No. 8,658,210, incorporated herein by reference.

FIELD OF INVENTION

The present invention relates to the field of drug delivery to a particular tissue within a subject, and more particularly to the field of the sustained release of a drug within a particular tissue within a subject.

BACKGROUND OF INVENTION

Several treatments have been developed to deliver therapeutic agents to a subject to treat an illness or a condition or for pain management. In most instances these therapeutic agents are delivered through a controlled or sustained release mechanism. Some systems to deliver sustained release doses of a therapeutic agent to a subject use biodegradable materials, such as polymeric matrices, containing the therapeutic agent. The matrices may be composed of biodegradable microparticles or microcarriers containing the therapeutic agent. As the microparticles or microcarriers degrade within a biological environment, they release the therapeutic agent at a controlled rate. One suitable biodegradable polymer is poly(lactic-co-glycolic acid) (PLGA). However, PLGA typically has a short degradation time and the time release of the therapeutic agents from a matrix formed with the PLGA is not readily tunable over a broad range. Additionally, PLGA degrades to form a high concentration of low molecular weight, acidic species. This interferes with the PLGA polymer matrices' biocompatibility and compatibility with therapeutic agents, as many are acid-sensitive. Another drawback to PLGA polymer matrices is that they cannot be tuned for their mechanical properties such as degree of crystallinity or glass transition temperature over a substantial range. This limits their ability to tune retention and mechanical compatibility with different tissues within a subject. Lastly, PLGA is not soluble in highly biocompatible alcohol solvents, such as ethanol, requiring stronger organic solvents which can have less tissue compatibility.

SUMMARY OF INVENTION

Embodiments of a therapeutic agent delivery system comprising a specific type of poly(ester amide) (PEA), a therapeutic agent and a water miscible solvent are herein disclosed. A method of delivering a therapeutic agent by delivering a therapeutic agent delivery system composed of a PEA polymer, a therapeutic agent and a water miscible solvent (to a physiological environment) of the therapeutic agent delivery system to form a membrane from the polymer to contain the therapeutic agent within the physiological environment is also described. An alternative method of delivering a therapeutic agent by delivering the same therapeutic agent delivery system to form a phase inversion depot composed of the PEA polymer and therapeutic agent is also described. Additionally, a kit including a syringe and a therapeutic agent delivery system within the syringe is also described.

DETAILED DESCRIPTION

In the following description, numerous embodiments are described in order to provide a thorough understanding of the present invention. One of ordinary skill in the art will understand that these embodiments are illustrative only and do not limit the scope of the present invention. Additionally, in other instances, known processing techniques and equipment have not been set forth in particular detail as they are known to those skilled in the art.

An embodiment of a therapeutic agent delivery system formed of a specific type of poly(ester amide) (PEA), a therapeutic agent and a water miscible solvent is described herein. A method of delivering the therapeutic agent by delivering the therapeutic agent delivery system formed of a PEA polymer, a therapeutic agent and a water miscible solvent to a physiological environment and causing phase separation of the therapeutic agent delivery system to form a membrane from the polymer to contain the therapeutic agent within the physiological environment is also described. Additionally disclosed is a kit including a syringe and a therapeutic agent delivery system within the syringe.

The therapeutic agent delivery system can include a specific type of PEA selected from one of the families of PEAs described below. The use of PEAs in therapeutic agent delivery systems can provide several advantages. For example, PEAs are composed of endogenous components and therefore endogenous enzymes can break them down. In addition, the degradation rates of PEAs can be controlled through varying the components or the stoichiometry of the components used for forming PEAs. Moreover, the mechanical properties of PEAs, and the depots formed from them, can be varied over a broad range. PEA variations will be described below in more detail. The ability to control PEA degradation rates in turn controls the therapeutic agent release rates from the therapeutic agent delivery system. The release rate can be tunable based upon which therapeutic agent is used. This can be accomplished by altering the composition of the PEA and by its molecular weight. The composition and the phase inversion dynamics of generating the depot will dictate the release rate. The release rates can be tuned to be hours, days or even months. For example, durations of release can include, but are not limited to, from about six hours to about six months, from about three days to about three months and from about one week to about one month. Useful PEA molecular weights are chosen to allow a suitable viscosity for the solution. Weight average molecular weight may be from 10,000 Daltons to 200,000 Daltons.

In some embodiments, the PEA is dissolved in a parenterally approved solvent. "Parenteral" means taken into the body or administered in a manner other than through the digestive tract, as by intravenous or intramuscular injection. The parenterally approved solvent can be completely or partially water miscible. Thus, upon introduction to a physiological environment, the solvent will diffuse out of the PEA leaving behind a membrane containing the therapeutic agent. Examples of parenterally approved solvents include, but are not limited to, ethanol, propylene glycol, benzyl benzoate, benzyl alcohol, n-methylpyrrolidone (NMP), and dimethyl sulfoxide (DMSO). In some embodiments, the combination of the PEA and the solvent may form a heterogeneous solution such as a colloidal suspension or an emulsion. In some embodiments, the combination of the PEA and the solvent may form a homogeneous solution. The amount of solvent mixed with the PEA varies depending on the amount of solvent needed to form a solution having a viscosity and rheology suitable for injection of the solution through a narrow gauge needle. The narrow gauge needle may have a gauge in a range of approximately 23 gauge to 27 gauge, more particularly, 24 gauge.

The therapeutic agent can be any entity capable of contributing to a therapeutic effect, a prophylactic effect, both a therapeutic and prophylactic effect, or any other biological effect that may be beneficial to a mammal. The agent can also have diagnostic properties. For example, the therapeutic agent can be a pharmaceutical agent, a biologic or an image-enhancing agent or any combination thereof.

In some embodiments, the therapeutic agent is a biologic. Biologics include, but are not limited to, cells, nucleotides, oligonucleotides, polynucleotides, polyoligonucleotides, amino acids, peptides, oligopeptides, polypeptides, proteins and antibodies. In one example, the biologic inhibits the activity of vascular smooth muscle cells. In another example, the biologic controls migration or proliferation of smooth muscle cells to inhibit restenosis. "Restenosis" refers to the reoccurrence of stenosis in a vessel after it has been treated with apparent success.

Therapeutic agents include, but are not limited to, antiproliferatives, anti-neoplastics, anti-mitotics, anti-inflammatories, anti-platelets, anti-coagulants, anti-fibrins, antithrombins, anti-biotics, anti-allergics, anti-oxidants, anti-migratories and any prodrugs, metabolites, analogs, homologues, congeners, derivatives, salts and combinations thereof. It is to be appreciated that one skilled in the art should recognize that some of the groups, subgroups, and individual therapeutic agents may not be used in some embodiments of the present invention.

Antiproliferatives include, for example, actinomycin D, actinomycin IV, actinomycin $I_1$, actinomycin $X_1$, actinomycin $C_1$, and dactinomycin (COSMEGEN®, Merck & Co., Inc.). Antineoplastics or antimitotics include, for example, paclitaxel (TAXOL®, Bristol-Myers Squibb Co.), docetaxel (TAXOTERE®, Aventis S.A.), methotrexate, azathioprine, vincristine, vinblastine, fluorouracil, doxorubicin hydrochloride (ADRIAMYCIN®, Pfizer, Inc.) and mitomycin (MUTAMYCIN®, Bristol-Myers Squibb Co.), and any prodrugs, metabolites, analogs, homologues, congeners, derivatives, salts and combinations thereof. Antiplatelets, anticoagulants, antifibrin, and antithrombins include, for example, sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors (ANGIOMAX®, Biogen, Inc.), and any prodrugs, metabolites, analogs, homologues, congeners, derivatives, salts and combinations thereof. Cytostatic or antiproliferative agents include, for example, angiopeptin, angiotensin converting enzyme inhibitors such as captopril (CAPOTEN® and CAPOZIDE®, Bristol-Myers Squibb Co.), cilazapril or lisinopril (PRINIVIL® and PRINZIDE®, Merck & Co., Inc.); calcium channel blockers such as nifedipine; colchicines; fibroblast growth factor (FGF) antagonists, fish oil (omega 3-fatty acid); histamine antagonists; lovastatin (MEVACOR®, Merck & Co., Inc.); monoclonal antibodies including, but not limited to, antibodies specific for Platelet-Derived Growth Factor (PDGF) receptors; nitroprusside; phosphodiesterase inhibitors; prostaglandin inhibitors; suramin; serotonin blockers; steroids; thioprotease inhibitors; PDGF antagonists including, but not limited to, triazolopyrimidine; and nitric oxide, and any prodrugs, metabolites, analogs, homologues, congeners, derivatives, salts and combinations thereof. Antiallergic agents include, but are not limited to, pemirolast potassium (ALAMAST®, Santen, Inc.), and any prodrugs, metabolites, analogs, homologues, congeners, derivatives, salts and combinations thereof.

Other therapeutic agents useful in the present invention include, but are not limited to, free radical scavengers; nitric oxide donors; rapamycin; everolimus; tacrolimus; 40-O-(2-hydroxy)ethyl-rapamycin; 40-O-(3-hydroxy)propyl-rapamycin; 40-O-[2-(2-hydroxy)ethoxy]ethyl-rapamycin; tetrazole containing rapamycin analogs such as those described in U.S. Pat. No. 6,329,386; estradiol; clobetasol; idoxifen; tazarotene; alpha-interferon; host cells such as epithelial cells; genetically engineered epithelial cells; dexamethasone; and, any prodrugs, metabolites, analogs, homologues, congeners, derivatives, salts and combinations thereof.

Free radical scavengers include, but are not limited to, 2,2',6,6'-tetramethyl-1-piperinyloxy, free radical (TEMPO); 4-amino-2,2',6,6'-tetramethyl-1-piperinyloxy, free radical (4-amino-TEMPO); 4-hydroxy-2,2',6,6'-tetramethyl-piperidene-1-oxy, free radical (TEMPOL), 2,2',3,4,5,5'-hexamethyl-3-imidazolinium-1-yloxy methyl sulfate, free radical; 16-doxyl-stearic acid, free radical; superoxide dismutase mimic (SODm) and any analogs, homologues, congeners, derivatives, salts and combinations thereof. Nitric oxide donors include, but are not limited to, S-nitrosothiols, nitrites, N-oxo-N-nitrosamines, substrates of nitric oxide synthase, diazenium diolates such as spermine diazenium diolate and any analogs, homologues, congeners, derivatives, salts and combinations thereof.

In some embodiments, the therapeutic agent can be an image-enhancing agent, which can include a radiopaque or MRI agent. "Radiopaque" refers to the ability of a substance to absorb x-rays. An MRI agent has a magnetic susceptibility that allows it to be visible with MRI. Representative radiopaque agents may include, but are not limited to, biodegradable metallic particles and particles of biodegradable metallic compounds such as biodegradable metallic oxides, biocompatible metallic salts and fluorinated dyes. Iodinated radiopaque agents may include, but are not limited to, acetriozate, diatriozate, iodimide, ioglicate, iothalamate, ioxithalamate, selectan, uroselectan, diodone, metrizoate, metrizamide, iohexol, ioxaglate, iodixanol, lipidial, ethiodol and combinations thereof. Examples of MRI agents include, but are not limited to, iron oxide, superparamagnetic iron oxide, and gadolinium salts such as gadodiamide, gadopentetate, gadoteridol and gadoversetamide.

The poly(ester amides) that can be included in the therapeutic agent delivery system may be from one of several families of PEAs. In one family, the PEA is composed of a diacid, a diol and at least one amino acid. The diacid is preferably a C2 to C12 diacid and is either aliphatic or unsaturated. The diol is also C2 to C12 and may include branching and unsaturation. A triol such as glycerol may also be added to the formulation to induce mild crosslinking in an embodiment where the formulation has a low solid percentage. The first amino acid may be glycine, valine, alanine, leucine, isoleucine or phenylalanine. An optional second amino acid may also be included that may contain a reactive side group for the attachment of pharmacologically active compounds or property modifiers. The second amino acid may be lysine, tyrosine, glutamic acid, or cysteine. This PEA family may also contain an optional hydrophilic diol or diamine for property modification. This component may be in the polymer backbone or attached as a pendant group. This optional diol or diamine may be, for example, polyethylene glycol (PEG), polypropyleneglycol (PPG), polyvinylpyrrolidone (PVP), hydroxyethylmethacrylate (HEMA), or hyaluronic acid.

In another family, PEAs based on amide diols may also be used in the therapeutic delivery system. In the structure of a PEA based on an amide diol, a diamine such a putrescine or cadaverene is endcapped with a hydroxyacid such as glycolic acid or lactic acid. The hydroxyl-terminated amide diol then reacts with a diacid either by transesterification or through an activated form such as an acid chloride.

The therapeutic agent delivery system that includes the poly(ester amide), the therapeutic agent, and the water-miscible solvent can be delivered to a treatment site within a physiological environment. Once delivered, the therapeutic agent delivery system phase separates to form a membrane of poly(ester amide) containing the therapeutic agent within the physiological environment. The therapeutic agent is trapped within the PEA membrane and will diffuse out of the membrane over a pre-determined time period as the PEA degrades. Therapeutic agent release may be linear or pulsed.

In some embodiments, the therapeutic agent delivery system may be delivered to the physiological environment by site-specific delivery with a catheter. Examples of catheters that may be used include needle catheters and balloon catheters. The site-specific injection may be, but is not limited to, used to treat vulnerable plaque, diabetes, pain management, arthritis, or coronary artery disease. Other treatment sites to which the therapeutic agent delivery system may be injected are known to those skilled in the art. In some embodiments, the therapeutic agent delivery system may be delivered to a treatment site within a physiological environment by syringe injection.

The therapeutic agent delivery system may be part of a kit that includes a catheter or a syringe. In some embodiments, the kit can include a syringe and a therapeutic agent delivery system comprising a PEA polymer, a therapeutic agent and a solvent contained within the syringe. The syringe may have a fine gauge needle having a gauge in a range of approximately 23 gauge to 27 gauge.

The synthesis of at least two families of PEAs is herein described. The term "poly(ester amide)" or "PEA" is defined as a condensation copolymer having at least one ester bond (I) and at least one amide bond (II):

$$-C-O-C- \quad (I)$$
$$\phantom{-C-}\|\phantom{O}\|$$
$$\phantom{-C-O-}O$$

$$-NH-C- \quad (II)$$
$$\phantom{-NH-}\|$$
$$\phantom{-NH-}O$$

The term "condensation copolymer" is defined as a copolymer that is a product of a process of polycondensation of two monomers. "Polycondensation" is defined in accordance with the definition used by the IUPAC (the International Union for Pure and Applied Chemistry." The IUPAC defines "polycondensation" as a process of polymerization in which the growth of polymer chains proceeds by condensation reactions between molecules of all degrees of polymerization (Definition 3.7). A "condensation reaction" is a chemical reaction in which two molecules or moieties react and become covalently bonded to one another by the concurrent loss of a small molecule, often water, methanol, or a type of hydrogen halide such as hydrochloric acid.

The synthetic techniques that can be used for obtaining the PEAs are described below. Generally, one reagent of group A and one reagent of group B react to form PEAs. According to some embodiments, the reagents of group A include various diol-diamines, and the reagents of group B include various dicarboxylic acids. In some embodiments, the coating can be free from any specific poly(ester amide). The reagents of groups A and B are characterized as follows.

A. Group A Reagents—Diol-Diamines

The diol-diamines comprising group A reagents that can be used according to embodiments of the present invention are chemical compounds having a general formula (III):

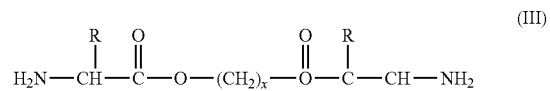

wherein R can be hydrogen, methyl, iso-propyl, sec-butyl, iso-butyl, benzyl, methyl mercaptoethyl ($CH_2-CH_2-S-CH_3$), methylene amide ($CH_2-CO-NH_2$), or ethylene amide ($CH_2-CH_2-CO-NH_2$), and x can be an integer between 2 and 16.

The reagents described by formula (III) are diol-diamines that can be synthesized by condensation of an amino acid and a diol. The synthesis can be carried under the conditions favoring esterification of the amino acid via the amino acid's carboxyl group. The reaction can be conducted under dehydrating conditions, which include anhydrous environment and an elevated temperature, for example, about 50° C. to about 120° C. The reaction can be catalyzed by a strong acid or base, e.g., p-toluenesulfonic acid Anhydrous conditions can be obtained by the removal of water via azeotropic distillation of the reaction solvent, e.g., toluene or benzene.

Diols that can be used to make diol-diamines having formula (III) have the formula $HO-(CH_2)_x-OH$, where x is defined above. Representative examples of diols that can be used include ethylene glycol, 1,2-propanediol, 1,3-propanediol, 1,4-butane diol, 1,5-pentanediol, 1,6-hexanediol, 1,7-heptanediol, 1,8-octanediol, 1,9-nonanediol, 1,10-decanediol, 1,11-undecanediol, 1,12-dodecanediol or mixtures thereof.

Amino acids that can be used to prepare diol-diamines having formula (III) have the formula $H_2N-CHR-COOH$, where R is defined above. Table 1 sets out some of these amino acids.

TABLE 1

| | | Amino Acid ($H_2N-CHR-COOH$) | |
|---|---|---|---|
| No. | R | Formula | Name |
| 1 | H | $H_2N-CH_2-COOH$ | glycine (aminoethanoic acid) |
| 2 | $CH_3$ | $H_2N-CH(CH_3)-COOH$ | alanine (2-aminopropanoic acid) |
| 3 | i-$C_3H_7$ | $H_2N-CH(CH(CH_3)_2)-COOH$ | valine (2-amino-3-methyl butyric acid) |
| 4 | sec-$C_4H_9$ | $H_2N-CH(CH(CH_3)CH_2CH_3)-COOH$ | isoleucine (2-amino-3-methyl pentanoic acid) |
| 5 | i-$C_4H_9$ | 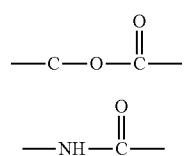 | leucine (2-amino-4-methyl pentanoic acid) |

TABLE 1-continued

Amino Acid (H$_2$N—CHR—COOH)

| No. | R | Formula | Name |
|---|---|---|---|
| 6 | C$_6$H$_5$—CH$_2$ | C$_6$H$_5$—CH$_2$—CH(NH$_2$)—COOH | phenylalanine (2-amino-3-phenyl-propanoic acid) |
| 7 | (CH$_2$)$_2$—S—CH$_3$ | CH$_2$—CH$_2$—S—CH$_3$ on CH with H$_2$N—CH—COOH | methionine (α-amino-γ-methyl-mercapto-butyric acid) |
| 8 | CH$_2$—CO—NH$_2$ | CH$_2$—CO—NH$_2$ on CH with H$_2$N—CH—COOH | asparagine (2,4-diamino-4-oxobutanoic acid) |
| 9 | (CH$_2$)$_2$—CO—NH$_2$ | CH$_2$—CH$_2$—CO—NH$_2$ on CH with H$_2$N—CH—COOH | glutamine (2,5-diamino-4-oxopentanoic acid) |

In addition to the amino acids listed in Table 1, other amino acids, e.g., proline (2-pyrrolidine carboxylic acid), can be used.

Either one amino acid or two different amino acids can be used to synthesize diol-diamines having formula (III). If one amino acid is used, it is present at two molar equivalents of the amino acid per one molar equivalent of the diol described above. If two different amino acids are used, they may be present at one molar equivalent of the first amino acid plus one molar equivalent of a second amino acid per one molar equivalent of a diol. They may also be present at different ratios so long as they add up to two equivalents based on one equivalent of diol. When using two amino acids at any ratio, up to three different diol-diamine products are possible.

B. Group B Reagents—Dicarboxylic Acids

Useful dicarboxylic acids composing group B reagents are compounds having a general formula (IV)$_1$:

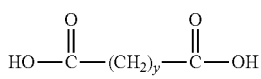

(IV)$_1$ wherein y can be an integer between 0 and 16. Some examples of dicarboxylic acids described by formula (IV) are summarized in Table 2. Mixtures of the carboxylic acids presented in Table 2 can be also used, if desired.

TABLE 2

Dicarboxylic Acid (HOOC—(CH$_2$)$_y$—COOH)

| No. | y | Formula | Name |
|---|---|---|---|
| 1 | 0 | HOOC—COOH | oxalic (ethanedioic) acid |
| 2 | 1 | HOOC—CH$_2$—COOH | malonic (propanedioic) |
| 3 | 2 | HOOC—(CH$_2$)$_2$—COOH | succinic (butanedioic) acid |
| 4 | 3 | HOOC—(CH$_2$)$_3$—COOH | glutaric (pentanedioic) acid |
| 5 | 4 | HOOC—(CH$_2$)$_4$—COOH | adipic (hexanedioic) acid |
| 6 | 5 | HOOC—(CH$_2$)$_5$—COOH | pimelic (heptanedioic) acid |
| 7 | 6 | HOOC—(CH$_2$)$_6$—COOH | suberic (octanedioic) acid |
| 8 | 7 | HOOC—(CH$_2$)$_7$—COOH | azelaic (nonanedioic acid) |
| 9 | 8 | HOOC—(CH$_2$)$_8$—COOH | sebacic (decanedioic) acid |
| 10 | 9 | HOOC—(CH$_2$)$_9$—COOH | nonane-1,9-dicarboxylic (undecanedioic) acid |
| 11 | 10 | HOOC—(CH$_2$)$_{10}$—COOH | decane-1,10-dicarboxylic (dodecanedioic) acid |
| 12 | 11 | HOOC—(CH$_2$)$_{11}$—COOH | brassylic (tridecanedioic) acid |
| 13 | 12 | HOOC—(CH$_2$)$_{12}$—COOH | dodecane-1,12-dicarboxylic (tetradecane dioic) acid |
| 14 | 13 | HOOC—(CH$_2$)$_{13}$—COOH | tridecane-1,13-dicarboxylic (pentadecanedioic) acid |
| 15 | 14 | HOOC—(CH$_2$)$_{14}$—COOH | thapsic (hexadecanedioic) acid |

Other dicarboxylic acids composing group B reagents are compounds having a general formula (IV)$_2$:

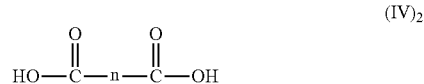

(IV)$_2$ wherein n can be a straight-chain or branched aliphatic moiety with 0 to 16 carbon atoms, any alkene moiety with 2 to 16 carbon atoms or any aromatic moiety with 6 to 12 carbon atoms. Examples include, but are not limited to, terephthalic acid, isophthalic acid and phthalic acid in addition to 1,4-, 1,3-, and 1,2-phenylenediacetic acid.

As mentioned above, to synthesize the PEAs, at least one reagent of group A can be reacted with at least one reagent of group B. Coupling the diol-diamines directly with the dicarboxylic acids can be accomplished by using acid or catalysis under dehydrating conditions. To conduct the coupling process with fewer side reactions, the dicarboxylic acid can be preliminarily activated with a carbodiimide, such as 1,3-dicyclohexylcarbodiimide (DCC), or 1-(3-dimethylaminopropyl)-3-ethylcarbodiimide hydrochloride (EDC). Alternatively, instead of a dicarboxylic acid, a derivative thereof, such as a diacid chloride, diacid bromide, or a p-nitrophenol derivative, can be used.

According to one embodiment, as a result of the synthesis, biologically absorbable PEAs having general formula (V) can be obtained:

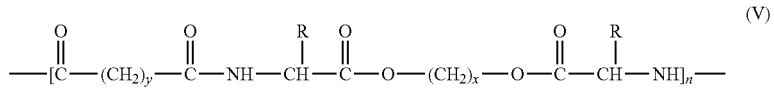

(V)

wherein R, x, and y are as defined above, and n is an integer having a value between about 35 and about 1100, for example, between 90 and 650.

According to another embodiment, if the amino acid that is used is proline, biologically absorbable PEAs having a general formula (VI) can be obtained:

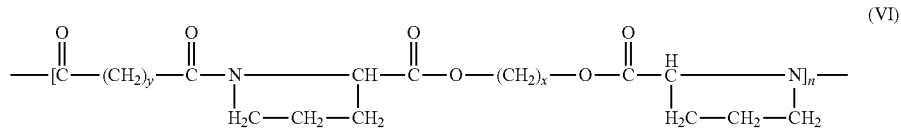

(VI)

wherein x, y, and n are as defined above.

One example of the synthesis of poly(ester amide) having general formula (V), is the synthesis the poly(ester amide) based on alanine, adipic acid, and 1,6-hexanediol according to the following procedure.

First, two equivalents of L-alanine can be combined in the benzene solution with one equivalent of 1,6-hexanediol, and with at least two equivalents of p-toluenesulfonic acid. Instead of benzene, toluene or chloroform can be used, if desired. The mixture can be heated to reflux and azeotropically distilled using a Dean-Stark trap to remove water. As a result, the di-p-toluenesulfonic acid salt of the bis-(L-alanine)-1,6-hexylene diester (monomer 1) can be obtained.

Next, adipic acid can be activated by reacting one equivalent of adipoyl chloride with two equivalents of p-nitrophenol, in a tetrahydrofuran (THF) solution, with at least two equivalents of triethylamine, to obtain di-p-nitrophenyl adipate (monomer 2). Instead of THF, diethylether or p-dioxane can be used, if desired. Both monomer 1 and monomer 2 can have stoichiometries of about to 1:1. The closer the stoichiometry is to a ratio of 1:1, the higher the molecular weight of the polymer.

Finally, one equivalent of monomer 1 can be reacted with one equivalent of monomer 2 and at least two equivalents of triethylamine in dry N,N-dimethylacetamide (DMAC). Alternatively, dimethylformamide (DMF) or dimethylsulfoxide (DMSO) can be used instead of DMAC. The ratio of monomers 1 and 2 can, but need not, be 1:1. Generally, the molar ratio of the two monomers is within 10% of each other, depending on the desired molecular weight of the final polymer. The ratio can deviate from 1:1, but in case of deviation the polymerization may stop at a lower molecular weight.

After combining the reactants at room temperature, the mixture can be heated with stirring at about 80° C. for about 16 hours. The viscous reaction mixture can be cooled to room temperature, diluted with a quantity of alcohol (such as methanol or ethanol), and poured into water. As a result, the final polymer, co-poly-[N,N'-adipoyl-bis-(L-alanine)-1,6-hexylene diester] can be produced. The precipitated polymer can be isolated, washed with water, and dried under vacuum.

EXAMPLES

The following examples are provided to further illustrate embodiments of the present invention.

Example 1

A copolymer, co-poly-{N,N'-sebacoyl-bis-(L-leucine)-1,6-hexylene diester}, having formula (VII) can be synthesized and used in the practice of the invention:

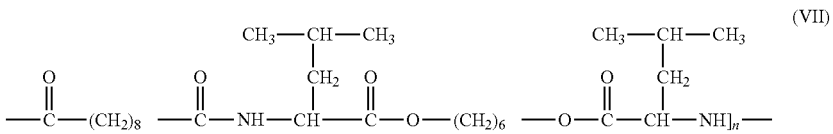

(VII)

wherein n can be between 85 and 95, for example, 90.

To synthesize the copolymer (VII), a diol-diamine substance of a family having formula (III) can be reacted with a dicarboxylic acid substance of a family having formula (IV).

The diol-diamine substance can be the di-p-toluenesulfonic acid salt of bis-(L-leucine)-1,6-hexylene diester and can be synthesized by condensation of L-leucine with 1,6-hexanediol using a p-toluenesulfonic acid catalyst.

The dicarboxylic acid substance can be the di-p-nitrophenyl derivative of sebacic acid, and can be synthesized by the condensation of p-nitrophenol with sebacoyl chloride. The conditions for the synthesis of the diol-diamine and the dicarboxylic acid substances can be determined by those having ordinary skill in the art.

The synthesis of copolymer (VII) can be carried out according to the following procedure. About 100.3 g (0.15 mole) of the di-p-toluenesulfonic toluenesulonic acid salt of bis-(L-leucine)-1,6-hexylene diester can be mixed with about 105 ml dry DMAC and can be reacted with about 66.67 g (0.15 mole) of di-p-nitrophenyl sebacinate. The reagents can be combined in a one-liter round bottom flask equipped with a mechanical stirrer, a nitrogen inlet and a heated oil bath, at room temperature.

About 46.2 ml (0.33 mole) of dry triethylamine can then be added to the flask, with stirring. The temperature of the reaction mixture can be increased to about 80° C., and the solution can be stirred for about 10 hours. The viscous reaction mixture can then be cooled to room temperature, diluted with about 250 ml of ethanol, and slowly added to about 2 liters of de-ionized water with stirring. The polymer can then be isolated by filtration, re-suspended in about 1 liter of deionized water, and again isolated by filtration. The process of re-suspension and filtration can be repeated. Finally, the polymer can be dried at about 30° C. under reduced pressure for between 8 hours and 24 hours.

Example 2

A copolymer, co-poly-{N,N'-sebacoyl-bis-(L-leucine)-1,4-butylene diester} having formula (VIII), can be synthesized and used in the practice of the invention:

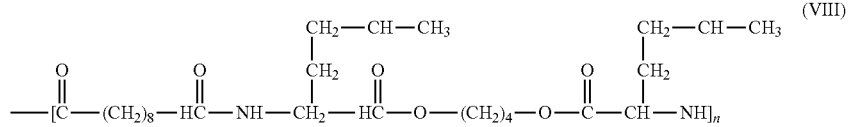

wherein n is between 140 and 160, for example, 150.

The copolymer (VIII) can be synthesized in the same manner as the copolymer (VII) described in Example 1, except the 1,4-butanediol derivative can be used instead of 1,6-hexanediol derivative. Specifically, the following synthetic procedure can be used.

About 99.13 g (0.15 mole) of the di-p-toluenesulfonic acid salt of bis-(L-leucine)-1,4-butylene diester can be mixed with about 105 ml dry DMAC and can be reacted with about 66.67 g (0.15 mole) of di-p-nitrophenyl sebacinate. The reagents can be combined in a 1-liter round bottom flask equipped with a mechanical stirrer, a nitrogen inlet and a heated oil bath, at room temperature.

About 46.2 ml (0.33 mole) of dry triethylamine can then be added to the flask, with stirring. The temperature of the reaction mixture can be increased to about 80° C., and the solution can be stirred for about 12 hours. The viscous reaction mixture can then be cooled to room temperature, diluted with about 250 ml of ethanol, and slowly added to about 2 liters of de-ionized water with stirring. The polymer can then be isolated by filtration, re-suspended in about 1 liter of deionized water, and again isolated by filtration. The process of re-suspension and filtration can be repeated. Finally, the polymer can be dried at about 30° C. under reduced pressure for between 8 hours and 24 hours.

Example 3

A copolymer, co-poly-{N,N'-adipoyl-bis-(L-leucine)-1,4-butylene diester} having formula (IX) can be synthesized and used in practice of the invention:

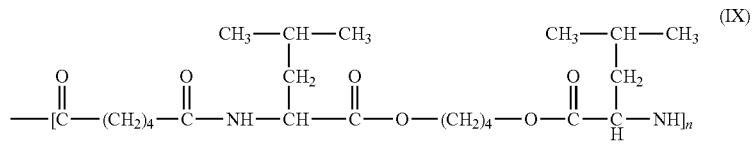

wherein n is between 140 and 160, for example, 150.

The copolymer (IX) can be synthesized using in the same manner as the copolymer (VIII) described in Example 2, except adipic acid can be used instead of sebacic acid. Specifically, the following synthetic procedure can be used.

About 99.13 g (0.15 mole) of the di-p-toluenesulfonic acid salt of bis-(L-leucine)-1,4-butylene diester can be mixed with about 76 ml dry DMAC and can be reacted with about 58.2 g (0.15 mole) of di-p-nitrophenyl adipate. The reagents can be combined in a 1-liter round bottom flask equipped with a mechanical stirrer, a nitrogen inlet and a heated oil bath, at room temperature.

About 46.2 ml (0.33 mole) of dry triethylamine can be then added to the flask, with stirring. The temperature of the reaction mixture can be increased to about 80° C., and the solution can be stirred for about 10 hours. The viscous reaction mixture can then be cooled to room temperature, diluted with about 220 ml of ethanol, and slowly added to about 2 liters of de-ionized water with stirring. The polymer can then be isolated by filtration, re-suspended in about 1 liter of deionized water, and again isolated by filtration. The process of re-suspension and filtration can then be repeated. Finally, the polymer can be dried at about 30° C. under reduced pressure for between 8 hours and 24 hours.

Example 4

A copolymer, co-poly-{N,N'-adipoyl-bis-(L-alanine)-1,4-butylene diester}, having formula (X) can be synthesized and used in practice of the invention:

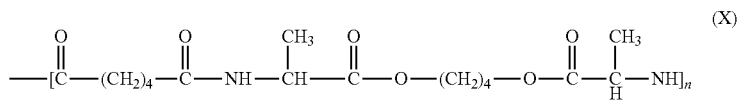

wherein n is between 250 and 300, for example, 275.

To synthesize copolymer (X), a diol-diamine substance of a family having formula (III) can be reacted with a dicarboxylic acid substance of a family having formula (IV).

The diol-diamine substance can be the di-p-toluenesulfonic acid salt of bis-(L-alanine)-1,4-butylene diester and can be synthesized by condensation of L-alanine with 1,4-butanediol using a p-toluenesulfonic acid catalyst.

The dicarboxylic acid substance can be the di-p-nitrophenyl derivative of adipic acid, and can be synthesized by the condensation of p-nitrophenol with adipoyl chloride.

The conditions for the synthesis of the diol-diamine and the dicarboxylic acid substances can be determined by those having ordinary skill in the art.

The synthesis of copolymer (X) can be carried out according to the following procedure. About 86.4 g (0.15 mole) of the di-p-toluenesulfonic acid salt of bis-(L-alanine)-1,4-butylene diester can be mixed with about 72 ml dry DMAC and can be reacted with about 58.2 g (0.15 mole) of di-p-nitrophenyl adipate. The reagents can be combined in a 1-liter round bottom flask equipped with a mechanical stirrer, a nitrogen inlet and a heated oil bath, at room temperature.

About 46.2 ml (0.33 mole) of dry triethylamine can then be added to the flask, with stirring. The temperature of the reaction mixture can be increased to about 80° C., and the solution can be stirred for about 16 hours. The viscous reaction mixture can then be cooled to room temperature, diluted with about 205 ml of ethanol, and slowly added to about 2 liters of de-ionized water with stirring. The polymer can then be isolated by filtration, re-suspended in about 1 liter of deionized water, and again isolated by filtration. The process of re-suspension and filtration can be repeated. Finally, the polymer can be dried at about 30° C. under reduced pressure for between 8 hours and 24 hours.

In one embodiment, a polymer used in preparing the composition is a PEA, which due to the labile nature of the ester groups, makes the PEA structure biodegradable. The PEA comprises at least one amide group and at least one ester group and, as a result, can have a wide variety of molecular configurations. Such a polymer can exhibit, for example, sufficient mechanical strength for stent coating applications and an ability to be broken down, absorbed, resorbed or otherwise eliminated by a mammal. For the purposes of the present invention, a polymer or coating is "biodegradable" when it is capable of being completely or substantially degraded or eroded when exposed to either an in vivo environment or an in vitro environment having physical, chemical, or biological characteristics substantially similar to those of an in vivo environment within a mammal. A polymer or coating is capable of being degraded or eroded when it can be gradually broken-down, resorbed, absorbed or eliminated by, for example, hydrolysis, enzymolysis, metabolic processes, bulk or surface erosion, and the like within a mammal. It should be appreciated that traces or residue of polymer may remain on the device following biodegradation. The terms "bioabsorbable" and "biodegradable" are used interchangeably in this application.

The polymers used in the present invention may be biodegradable and may include, but are not limited to, condensation copolymers. It should be appreciated, however, that polymers other than PEA may compose at least some percentage of the polymer component of the therapeutic agent delivery system. In some embodiments, these other polymers can also be blended or cross-linked with the PEA using, for example, an isocyanate or a diisocyanate. If these other polymers are also biodegradable, the amount incorporated should be limited by their effect on a required performance parameter of a product formed from the biodegradable polymer. Such performance parameters may include, for example, the mechanical strength of a coating or the rate of biodegradation and elimination of a coating from a mammal. If the other polymers are non-biodegradable, the polymer fragments produced during biodegradation should have molecular weights of a size that ensures elimination of the fragments from a mammal. In some embodiments, the molecular weight of the polymer fragments should be at or below about 40,000 Daltons, or any range therein. In other embodiments, the molecular weight of the fragments range from about 300 Daltons to about 40,000 Daltons, from about 8,000 Daltons to about 30,000 Daltons, from about 10,000 Daltons to about 20,000 Daltons, or any range therein.

Examples of polymers that can be combined with the PEA include, but are not limited to, polyacrylates such as poly(butyl methacrylate), poly(ethyl methacrylate), and poly(ethyl methacrylate-co-butyl methacrylate); fluorinated polymers or copolymers such as poly(vinylidene fluoride) and poly(vinylidene fluoride-co-hexafluoro propene); poly(N-vinyl pyrrolidone); poly(hydroxyvalerate); poly(L-lactic acid); polycaprolactone; poly(lactide-co-glycolide); poly(hydroxybutyrate); poly(hydroxybutyrate-co-valerate); polydioxanone; polyorthoester; polyanhydride; poly(glycolic acid); poly(D,L-lactic acid); poly(glycolic acid-co-trimethylene carbonate); polyphosphoester; polyphosphoester urethane; poly(amino acids); cyanoacrylates; poly(trimethylene carbonate); poly(iminocarbonate); co-poly(ether-esters); polyalkylene oxalates; polyphosphazenes; biomolecules such as fibrin, fibrinogen, cellulose, starch, collagen and hyaluronic acid; polyurethanes; silicones; polyesters; polyolefins; polyisobutylene and ethylene-alphaolefin copolymers; vinyl halide polymers and copolymers such as polyvinyl chloride; polyvinyl ethers such as polyvinyl methyl ether; polyvinylidene chloride; polyacrylonitrile; polyvinyl ketones; polyvinyl aromatics such as polystyrene; polyvinyl esters such as polyvinyl acetate; copolymers of vinyl monomers with each other and olefins such as poly(ethylene-co-vinyl alcohol) (EVAL), ethylene-methyl methacrylate copolymers, acrylonitrile-styrene copolymers, ABS resins, and ethylene-vinyl acetate copolymers; polyamides such as Nylon 66 and polycaprolactam; alkyd resins; polycarbonates; polyoxymethylenes; polyimides; polyethers; epoxy resins; polyurethanes; rayon; rayon-triacetate; cellulose; cellulose acetate; cellulose butyrate; cellulose acetate butyrate; cellophane; cellulose nitrate; cellulose propionate; cellulose ethers; and carboxymethyl cellulose.

PEA-Agent Combinations

The therapeutic agents of the present invention can be connected to a PEA as a pendant group or as an in-chain group, or be physically blended with the PEA polymer. It should be appreciated that the agent can be a polymeric agent, which can be attached as a pendant group or as an in-chain group.

I. The Agent as a Pendant Group

A polymer of the present invention can comprise a polymeric moiety having an A-moiety (A), a B-moiety (B), and an optional linkage ($L_1$) connecting A to B. The remainder of the polymer comprises an agent (X), and a linkage ($L_2$) connecting X to the polymer. This PEA-therapeutic agent combination can be generally represented by a formula (XI):

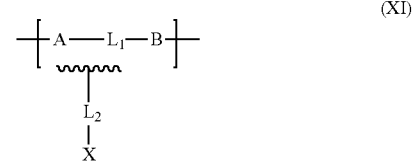

(XI)

In formula (XI), both A and B can be independently selected and comprise any combination of monomers such that the polymer has at least one ester group and one amide group. In some embodiments, the ester and amide are adjacent. Optionally, A and B can be connected by $L_1$, which can be a substituted, unsubstituted, hetero-, straight-chained, branched, cyclic, saturated or unsaturated aliphatic radical; and a substituted or unsubstituted aromatic radical. In some embodiments, $L_1$ can comprise from about 0 to about 50 carbon atoms, from about 2 to about 40 carbon atoms, from about 3 to about 30 carbon atoms, from about 4 to about 20 carbon atoms, from about 5 to about 10 carbon atoms, and any range therein. In other embodiments, the $L_1$ can alternately comprise a non-carbon species such as, for example, a disulfide. In other embodiments, R can comprise substituted or unsubstituted poly(alkylene glycols), which include, but are not limited to, PEG, PEG derivatives such as mPEG, poly(ethylene oxide), PPG, poly(tetramethylene glycol), poly(ethylene oxide-co-propylene oxide), or copolymers and combinations thereof. In one embodiment, the poly(alkylene glycol) is PEG. In another embodiment, the poly(alkylene glycol) may comprise a PEG derivative such as mPEG. In another embodiment, R can comprise a copolymer of PEG or a copolymer of a PEG derivative such as mPEG.

In some embodiments, X can also be optional and can be connected to the polymer by $L_2$, which can be any interunit linkage such as, for example, an ester, an anhydride, an acetal, an amide, a urethane, a urea, a glycoside, a disulfide, and a siloxane linkage. It is to be appreciated that one skilled in the art should recognize that some of these linkages may not be used in some embodiments of the present invention.

The selection of $L_2$ allows for control of the relative strength or stability of the bond between X and the polymeric moiety as compared to the strength or stability of the bonds within the polymeric moiety. Control over this relative strength or stability allows for release of therapeutic agents that are substantially free of attached molecules from the polymeric moiety. The agent X can be biobeneficial, bioactive, diagnostic or a have a combination of these characteristics, and is discussed in detail above.

In some embodiments, A can be represented by a formula (XII):

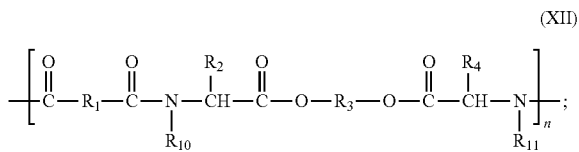

and in other embodiments, B can be represented by any of formulas (XIII)-(XV);

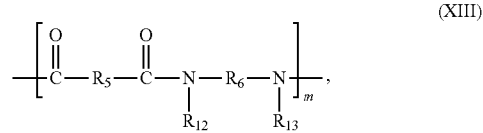

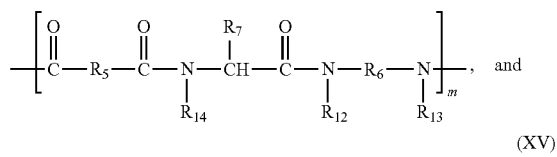

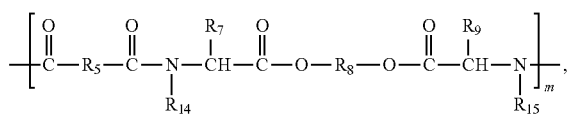

where $R_1$ and $R_5$ can be optional and can also be independently selected from a substituted, unsubstituted, hetero-, straight-chained, branched, cyclic, saturated or unsaturated aliphatic radical; or a substituted, unsubstituted, or hetero-aromatic radical; $R_3$ and $R_8$ can be independently selected from a substituted, unsubstituted, hetero-, straight-chained, branched, cyclic, saturated or unsaturated aliphatic radical; or a substituted, unsubstituted, or hetero-aromatic radical; $R_2$ and $R_4$ can be independently selected from a hydrogen; a substituted, unsubstituted, hetero-, straight-chained, branched, cyclic, saturated or unsaturated aliphatic radical; or a substituted, unsubstituted, or hetero- aromatic radical; $R_6$ can be selected from a substituted, unsubstituted, hetero-, straight-chained or branched aliphatic radical; $R_7$ and $R_9$ can be independently selected from a hydrogen; a substituted, unsubstituted, hetero-, straight-chained, branched, cyclic, saturated or unsaturated aliphatic radical; and a substituted or unsubstituted aromatic radical; $R_{10}$ through $R_{15}$ can be independently selected from a hydrogen; a substituted, unsubstituted, hetero-, straight-chained, branched, cyclic, saturated or unsaturated aliphatic radical; or a substituted, unsubstituted, or hetero- aromatic radical; m can range from about 4 to about 1400, from about 10 to about 800, from about 20 to about 400, or any range therein; n can range from about 3 to about 1400, from about 10 to about 800, from about 20 to about 400, or any range therein; and the sum of m and n and can range from about 30 to about 1600, from about 50 to about 1200, from about 75 to about 900, from about 100 to about 600, or any range therein. In some embodiments, groups $R_{10}$ through $R_{15}$ are limited to hydrogen. In other embodiments, $R_1$ is not equal to $R_5$.

The polymers of the present invention can generally be prepared in the following manner: a polyester-type adduct is prepared by combining an amino acid with a diol. In some embodiments, the amino acid is a bi-functional amino acid. The polyester adduct can be combined with a multi-functional amino acid, a diacid or derivative of a diacid, and an agent. In embodiments where a peptide-type adduct is desired, two amino acids can be independently selected and combined such as, for example, where one amino acid is bi-functional and the other is multi-functional. An example of a multi-functional amino acid is a tri-functional amino acid. Examples of tri-functional amino acids include, but are not limited to, lysine, tyrosine, arginine, or glutamic acid. Examples of diacids include, but are not limited to, the dicarboxylic acids listed above. Examples of derivatives of diacids include, but are not limited to, diacid chloride, a dianhydride, or a di-p-nitrophenyl ester. In the event that a dicarboxylic acid is used, the reaction may be carried out in the presence of 1-ethyl-3(3-dimethylaminopropyl) carbodiimide (EDC) or 1,3-dicyclohexylcarbodiimide (DCC) in a solvent such as dimethylformamide (DMF) or tetrahydrofuran (THF). If a diacid chloride or di-p-nitrophenyl ester is used, an excess of pyridine or triethylamine should be present. Examples of other solvents that may be used include, but are not limited to, dimethylacetamide (DMAC), dimethylsulfoxide (DMSO), acetone, and dioxane.

The reaction conditions should be anhydrous and favor esterification of the amino acid's carboxyl group. In some embodiments, the reaction solvents include toluene and benzene and should be distilled to remove water. The reaction can be catalyzed by a strong acid or base such as, for example, p-toluenesulfonic acid (TsOH). In some embodiments, the temperature of the reaction ranges from about 25° C. to about 150° C., from about 35° C. to about 100° C., from about 50° C. to about 80° C., or any range therein. In some embodiments, the reaction times range from about 1 hour to about 24 hours, from about 6 hours to about 18 hours, from about 10 hours to about 14 hours, or any range therein. Any agent described above can be used.

Trifunctional amino acids can be incorporated into the polymer by protecting the third functionality with a protecting group that is later removed. Examples of protecting groups are benzyl esters for the lysine carboxyl or t-butoxycarbonyl for amino groups such as, for example, the amino group in glutamic acid. In some embodiments, the amino acid that is selected to link with the agent is not lysine.

The benzyl ester protecting group may be removed from the lysine carboxyl by hydrogenolysis with hydrogen gas over a catalyst such as, for example, palladium or platinum on carbon. Examples of suitable solvents include, but are not limited to, ethanol, methanol, isopropanol, and THF. In some embodiments, the reaction may be conducted under about 1 atmosphere of hydrogen for about 6 hours to about 24 hours, for about 8 hours to about 16 hours, for about 10 hours to about 14 hours, or any range therein. After removal of the protecting group, an agent comprising an amino, a hydroxyl, a thiol, or a combination thereof is connected to the carboxyl group. Coupling agents used to connect the agent include, but are not limited to, EDC and DCC. Thionyl chloride or phosphorous pentachloride may be used in a less selective process of preparing the acid chloride derivative.

An amine functional compound such as, for example, 4-amino-TEMPO, may be connected to a polymer containing free carboxyls such as, for example, the lysine-derived carboxyls, by first activating the carboxyls and coupling the amine in a solvent under agitation. The carboxyls may be activated with, for example, N-hydroxysuccinimide (NHS) and DCC in a solvent such as, for example, THF or chloroform, which produces N-hydroxysuccinimidyl ester. Examples of the solvent that may be used to couple the amine to the carboxyls include, but are not limited to, THF and DMF. In some embodiments, the reaction occurs at a temperature ranging from about 5° C. to about 50° C., from about 15° C. to about 35° C., from about 20° C. to about 30° C., or any range therein. In some embodiments, the reaction time ranges from about 0.5 hours to about 24 hours, from about 1 hour to about 18 hours, from about 4 hours to about 16 hours, from about 6 hours to about 12 hours, or any range therein.

In one embodiment, a family of PEAs can be prepared by reacting a diol, a diacid, two independently selected amino acids, and an agent. The resulting product is PEA represented by a formula (XVI):

where the groups $R_1$ and $R_5$ can be optional and can also be independently selected substituted, unsubstituted, hetero-, straight-chained, branched, cyclic, saturated or unsaturated aliphatic radicals; or substituted or unsubstituted aromatic radicals. The group $R_3$ can be a substituted, unsubstituted, hetero-, straight-chained, branched, cyclic, saturated or unsaturated aliphatic radical; or a substituted, unsubstituted, or hetero- aromatic radical. The groups $R_2$ and $R_4$ can be independently selected hydrogens; substituted, unsubstituted, hetero-, straight-chained, branched, cyclic, saturated or unsaturated aliphatic radicals; or substituted or unsubstituted aromatic radicals. The group $R_6$ can be a substituted, unsubstituted, hetero-, straight-chained or branched aliphatic radical. The group X can be an agent; and n and m are integers not equal to 0.

Note, however, that in some embodiments, the polymers of the present invention do not comprise the following combination of the A-moiety, B-moiety, $L_2$, and X as represented by a formula (XVII):

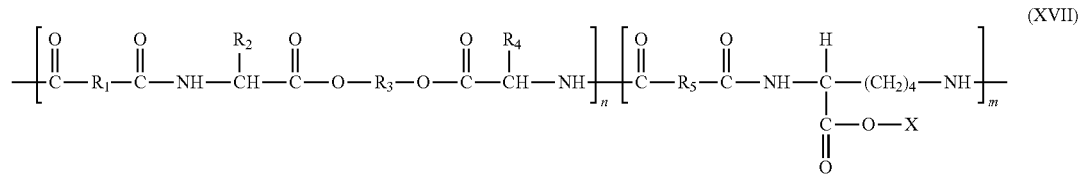

(XVII)

In formula (XVII), the groups $R_1$, $R_3$ and $R_5$ are independently selected, straight-chained or branched, saturated, aliphatic radicals having from 2-20 carbon atoms. The groups $R_2$ and $R_4$ are independently selected, straight-chained or branched, saturated, aliphatic radicals having from 1-6 carbon atoms; straight-chained or branched, aliphatic radicals having from 2-6 carbon atoms and at least one unsaturated carbon-carbon bond; straight-chained or branched, aliphatic radicals having from 2-6 carbon atoms and at least one carbon-carbon triple bond; phenyl radicals; an ortho-fused bicyclic carbocyclic radical having 6-10 carbon atoms and at least one aromatic ring; or hydrogen. The group X is a straight-chained or branched, saturated, aliphatic radical having from 1-6 carbon atoms; a phenyl radical; an ortho-fused bicyclic carbocyclic radical having 6-10 carbon atoms and at least one aromatic ring; or hydrogen. The subscripts m and n are integers not equal to 0.

In some embodiments of the present invention, diacids comprising epoxy groups may not be used to produce the PEAs. In other embodiments, diacids comprising epoxy groups may not be used to produce the PEAs where the amino acid chosen to link with X is lysine, and X is 4-amino-TEMPO or rapamycin. In other embodiments, $R_1$ and $R_5$ may not be substituted with epoxy groups where $R_1$ and $R_5$ are straight-chained-butylene or straight-chained-

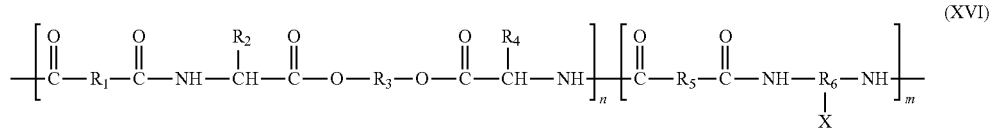

(XVI)

hexylene radicals. In other embodiments, $R_1$ and $R_5$ may not be substituted with epoxy groups where $R_1$ and $R_5$ are straight-chained-butylene or straight-chained-hexylene radicals, and X is TEMPO or rapamycin. In other embodiments, $R_1$ and $R_5$ may not be substituted with epoxy groups where $R_1$ and $R_5$ are straight-chained-butylene or straight-chained-hexylene radicals, when X is 4-amino-TEMPO or rapamycin, and $L_2$ is the following ester linkage prior to connecting X to $L_2$:

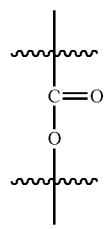 [SMILES: *OC(*)=O]

In other embodiments, $R_1$ and $R_5$ may not be substituted with epoxy groups where $R_1$ and $R_5$ are straight-chained-butylene or straight-chained-hexylene radicals, and (i) X is TEMPO and $L_2$ is

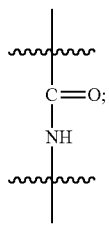

or, (ii) X is rapamycin and $L_2$ is

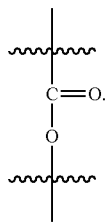

In other embodiments, a PEA may not be produced from a polycarboxylic acid that is 2,3-epoxysuccinic acid, 3,4-epoxyadipic acid or a diepoxyadipic acid, where the amino acid chosen to link with X is lysine, and X is 4-amino-TEMPO or rapamycin. In other embodiments, $R_1$ is not the same as $R_5$.

In formula (XVII), $L_2$ is an ester, which may be undesirable in some embodiments. As illustrated and described below, the careful selection of $L_2$ can help alleviate regulatory issues that may arise from the creation of derivatives of X during biodegradation of the polymers. Examples of $L_2$ include, but are not limited to, amides, esters, anhydrides, ketals, acetals, orthoesters and all-aromatic carbonates. In some embodiments, $L_2$ can be an ester, an anhydride, a ketal, an acetal, an orthoester, or an all-aromatic carbonates. In some embodiments, $L_2$ can be an anhydride, a ketal, an acetal, an orthoester or an all-aromatic carbonate. In some embodiments, $L_2$ can be a ketal, an acetal, an orthoester or an all-aromatic carbonate. In some embodiments, $L_2$ can be an acetal, an orthoester or an all-aromatic carbonate. In some embodiments, $L_2$ can be an orthoester or an all-aromatic carbonate. In some embodiments, $L_2$ can be an all-aromatic carbonate, which includes linkages comprising moieties represented by formula (XVIII):

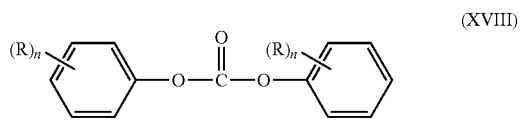

wherein R is optional and can be independently selected from, for example, a substituted, unsubstituted, hetero-, straight-chained, branched, cyclic, saturated and unsaturated aliphatic radicals; substituted and unsubstituted aromatic radicals; and combinations thereof. The subscript n is an integer not equal to 0.

In some embodiments, the PEA is represented by a formula (XIX):

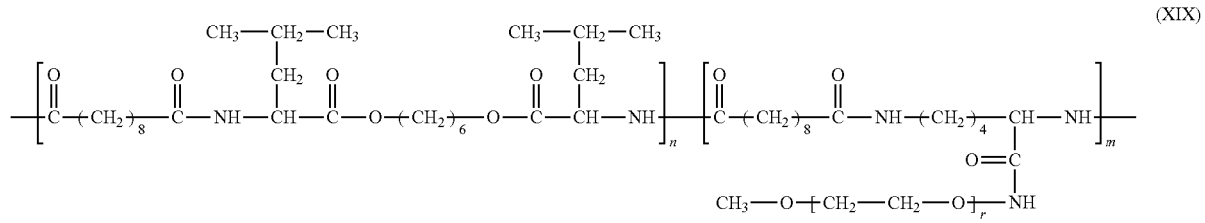

wherein n, m, and r are integers not equal to 0. In formula (XIX), the diol is hexane-1,6-diol, the diacid is sebacic acid, one amino acid is leucine, the other amino acid is lysine, and the agent is mPEG. The mPEG is connected to the B-moiety through an amide linkage, which is a stable linkage relative to the stability of the remainder of the polymer.

Formula (XX) represents a polymer with an amide linkage. Note, however, that in some embodiments, a PEA represented by formula (XX) is not within the scope of the present invention:

wherein n and m are integers not equal to 0. In formula (XXI), the diol is butane-1,6-diol, the diacid is sebacic acid, one amino acid is leucine, the other amino acid is lysine, and the agent is TEMPO. The TEMPO is connected to the B-moiety through an ester linkage, which is more labile than an amide linkage and allows for release of the agent from the polymer. The cleavage of the $L_2$ ester competes with the cleavage of the PEA esters and may result in attachment of additional molecules to the TEMPO that were derived from degradation of the polymer at ester linkages.

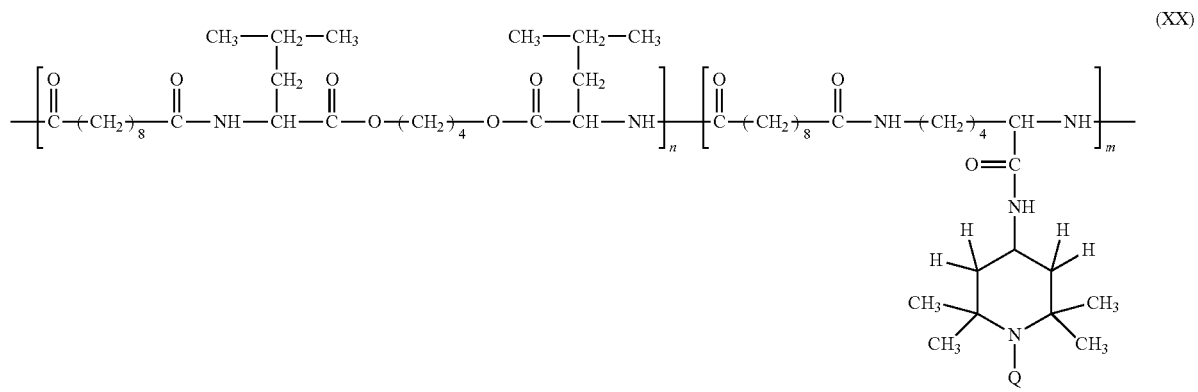
(XX)

wherein n and m are integers not equal to 0. In formula (XX), the diol is butane-1,6-diol, the diacid is sebacic acid, one amino acid is leucine, the other amino acid is lysine, and the agent is TEMPO. The TEMPO is connected to the B-moiety through an amide linkage, which may remain intact during biodegradation of the polymer resulting in attachment of additional molecules to the TEMPO that were derived from degradation of the polymer at the ester linkages. As a result, such a released agent would be a derivative of TEMPO rather than TEMPO and could cause regulatory concerns.

In some embodiments, the PEA is represented by a formula (XXI):

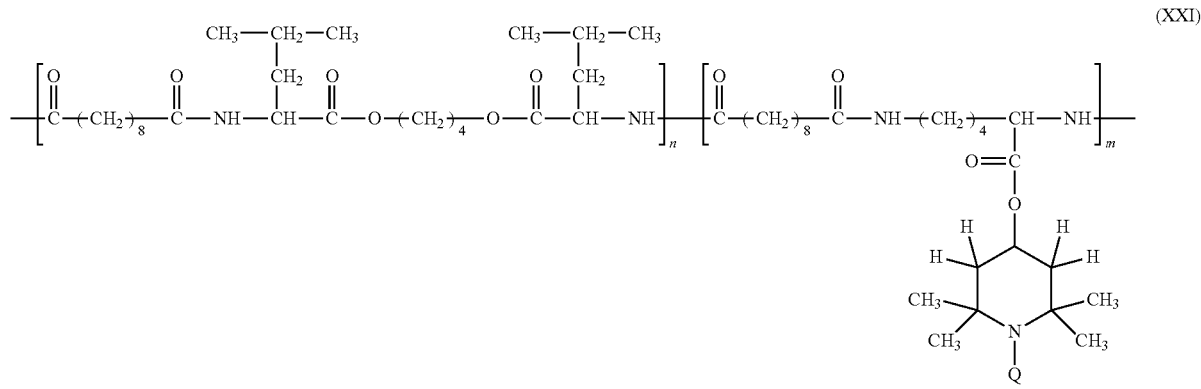
(XXI)

In some embodiments, the PEA is represented by a formula (XXII):

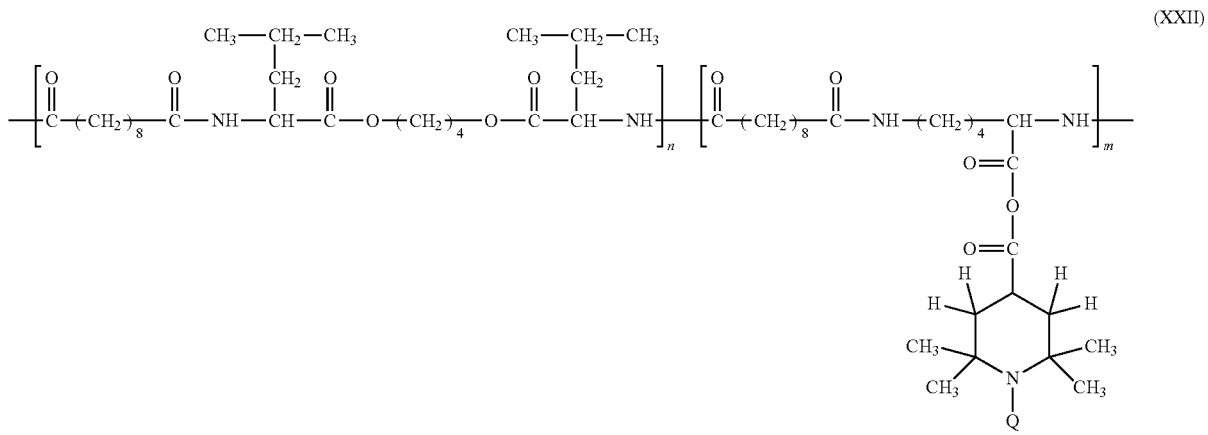

(XXII)

wherein n and m are integers not equal to 0. In formula (XXII), the diol is butane-1,6-diol, the diacid is sebacic acid, one amino acid is leucine, the other amino acid is lysine, and the agent is TEMPO. The TEMPO is connected to the B-moiety through an anhydride linkage, which is more labile than an ester linkage and, thus, may allow for release of the agent without attachment of additional molecules derived from biodegradation of the polymer at ester linkages.

In another embodiment, a family of PEAs comprising a dipeptide fragment can be prepared by reacting a diol, a diacid, two different amino acids, and an agent. The resulting product is a PEA represented by a formula (XXIII):

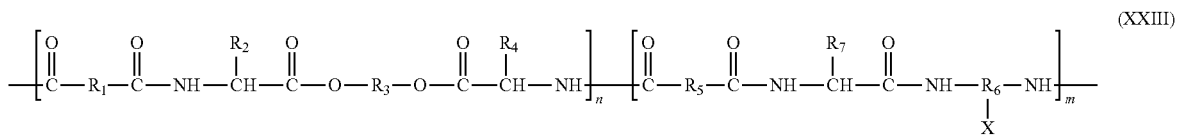

(XXIII)

wherein where $R_1$ and $R_5$ can be optional and can also be independently selected from a substituted, unsubstituted, hetero-, straight-chained, branched, cyclic, saturated or unsaturated aliphatic radical; or a substituted, unsubstituted, or hetero-aromatic radical; $R_3$ can be independently selected from a substituted, unsubstituted, hetero-, straight-chained, branched, cyclic, saturated or unsaturated aliphatic radical; or a substituted, unsubstituted, or hetero-aromatic radical; $R_2$, $R_4$ and $R_7$ can be independently selected from a hydrogen; a substituted, unsubstituted, hetero-, straight-chained, branched, cyclic, saturated or unsaturated aliphatic radical; or a substituted, unsubstituted, or hetero-aromatic radical; $R_6$ can be selected from a substituted, unsubstituted, hetero-, straight-chained or branched aliphatic radical; X can be an agent; m can range from about 4 to about 1400; n can range from about 3 to about 1400; and the sum of m and n and can range from about 30 to about 1600.

In some embodiments, the PEA is represented by a formula (XXIV):

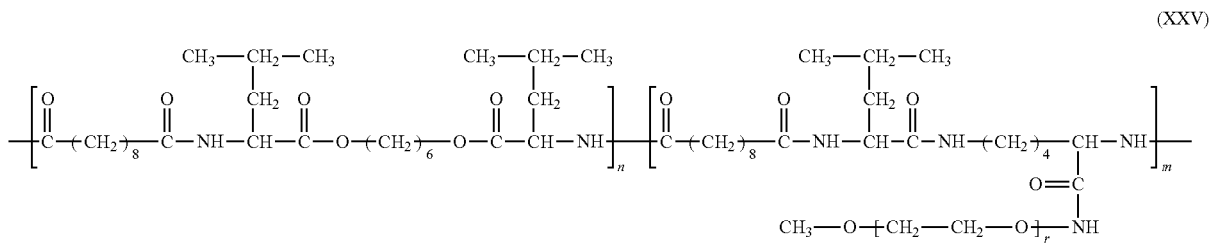

(XXV)

wherein n, m, and r are integers not equal to 0. In formula (XXIV), the diol is hexane-1,6-diol, the diacid is sebacic acid, one amino acid is leucine, the other amino acid is lysine, X is Mpeg and $L_2$ is an amide, which is stable relative to the stability of the remainder of the polymer.

In some embodiments, the PEA is represented by a formula (XXV):

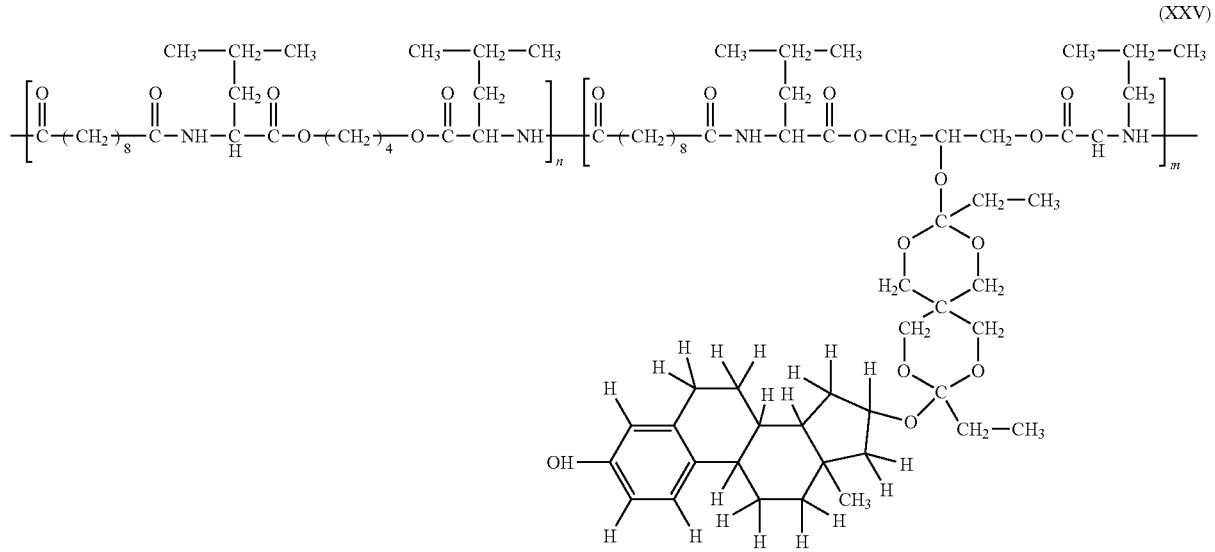

(XXV)

wherein n and m are integers not equal to 0. In formula (XXV), the diol is butane-1,4-diol, the diacid is sebacic acid, one amino acid is leucine, the other amino acid is lysine, X is estradiol and $L_2$ is an orthoester known as 3,9-diethylidene-2,4,8,10-tetraoxaspiro-[5,5]-undecane (DETOSU), which is more labile than an ester.

To make the polymer, an oligo- or polyester-type diamino adduct can be made as described above, combining leucine and butane-1,4-diol. One equivalent of glycerol can be combined with two equivalents of leucine to obtain an amino-terminated polymeric subunit. Next, the polyester-type diamino adduct can be combined with sebacic acid and the amino-terminated polymeric subunit to obtain a hydroxy-functional PEA. Estradiol then can be combined with 3,9-diethylidene-2,4,8,10-tetraoxaspiro-[5,5]-undecane (DETOSU) to form an estradiol-DETOSU adduct. The hydroxy-functional PEA can be reacted with the estradiol-DETOSU adduct to form the PEA-agent combination.

A polymeric agent such as, for example, heparin can be connected to a PEA as a graft-copolymer. A PEA with pendant amino groups on the polymer backbone may be produced by a method that comprises polymerizing bis-(L-leucine)-1,6-hexylene diester with di-p-nitrophenyl sebacate and ε-carbobenzoxy-L-lysine in a suitable solvent such as, for example, DMF or THF. The temperature of the reaction ranges from about 25° C. to about 150° C., from about 50° C. to about 125° C., from about 80° C. to about 100° C., or any range therein. The reaction occurs for a time ranging from about 1 hour to about 24 hours, from about 6 hours to about 18 hours, from about 10 hours to about 14 hours, or any range therein. The carbobenzoxy protecting group can be removed with hydrogenolysis over a palladium on carbon catalyst using the method described above. A heparin-aldehyde adduct can be connected by reductive amination using sodium cyanoborohydride ($NaCNBH_3$) and a DMF/water solvent.

II. Agent as a Polymeric Block

A polymeric agent can be connected to a PEA as a block-copolymer. Examples of agents that can be incorporated into PEAs as polymeric blocks include, but are not limited to, heparin, hyaluronic acid, and poly(ethylene glycol)(PEG).

1. PEAs Comprising Heparin or Hyaluronic Acid Block(s)

A block-copolymer of PEA and heparin can be prepared by combining an amino-terminated PEA with a heparin-aldehyde adduct. An example of a heparin-aldehyde adduct is represented by a formula (XXVI):

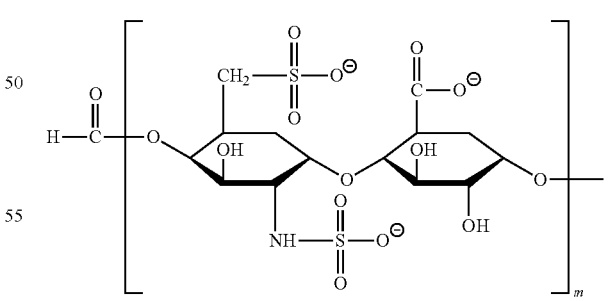

wherein m is an integer not equal to 0.

The heparin-aldehyde adduct can be combined with an amino-terminated PEA in a DMF/water solvent and subsequently reduced with $NaCNBH_3$ to produce the following PEA-heparin copolymer structure represented by formula (XXVII):

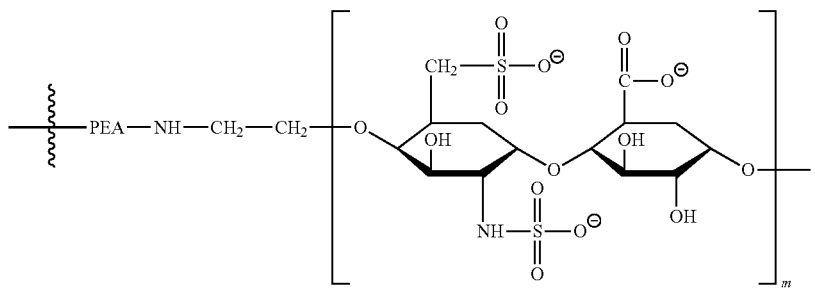

wherein m is an integer not equal to 0.

One method of preparing the amino-terminated PEA comprises deviating from a one-to-one stoichiometry between the sum of the amino-terminated subunits and the diacids or diacid derivatives. To achieve the highest molecular weight, the stoichiometry of the diacids or diacid derivatives is kept at one-to-one with the sum of the amino-terminated subunits, because an excess of either component results in an amino-terminated PEA with a lower molecular weight.

Another method of preparing the amino-terminated PEA comprises keeping a one-to-one stoichiometry between the amino-terminated subunits and the diacids or diacid derivatives and the polymerization is allowed to proceed for a predetermined length of time. The polymerization is terminated by the introduction of an excess of a reactive diamine such as, for example, 1,4-butanediamine. All carboxyl endgroups are terminated and any unreacted diacids or diacid derivatives are consumed. Any low molecular weight material can be separated from the polymer by precipitating the polymer in a suitable solvent known to one of skill in the art.

The PEA-heparin copolymer shown above is an AB-block copolymer. The AB-type copolymers result when the two polymers only have a single active end. The method of the present invention can be designed to produce an AB copolymer, an ABA copolymer or an ABABAB . . . multi-block copolymer by activating either one or both ends of the agent polymer and the PEA polymer. Copolymers of the ABA-type result where one polymer has one active end and the other polymer has two active ends. Copolymers of the ABABAB . . . -type result where both polymers have two active ends.

A block-copolymer of PEA and heparin can be prepared by combining a carboxyl-terminated PEA with a heparin-aldehyde adduct. The heparin is first activated with, for example, EDC or DCC and then combined with a large excess of adipic dihydrazide to prepare an amino-functionalized heparin. Alternatively, a heparin-aldehyde adduct can be treated with ammonia or n-butylamine in the presence of a reducing agent such as, for example, sodium borohydride (NaBH$_4$), potassium borohydride (KBH$_4$), or NaCNBH$_3$. The carboxyl-terminated PEA is activated with, for example, EDC or DCC, and combined with the amino-functional heparin.

It should be appreciated that, in some embodiments of the present invention, the agent may be any biobeneficial agent that can enhance the biocompatibility or non-fouling properties of a PEA polymer. For example, hyaluronic acid can be a polymeric agent used to form a PEA-hyaluronic acid copolymer. Hyaluronic acid has free carboxyl groups, so a hyaluronic acid-aldehyde adduct can be made, for example, by oxidizing hyaluronic acid with nitrous acid or periodate. The hyaluronic-acid-aldehyde adduct can then be combined with a PEA as described above.

A PEA that is both carboxyl-terminated and amino-terminated can be analyzed using standard analytical techniques to determine a ratio of carboxyl groups to amino groups. Knowing this ratio will allow one skilled in the art to decide whether to connect the polymer agent to the amino ends of the PEA or to the carboxyl ends of the PEA. A skilled artisan can protect the amino groups on the PEA with, for example, acetic anhydride to reduce undesirable side conjugation when combining a carboxyl-terminated PEA with a heparin-aldehyde adduct.

2. Poly(ethylene glycol) Block(s)-Containing PEAs

A block copolymer of PEA and PEG can be prepared using a variety of techniques. In one embodiment, an amino-terminated PEA can be combined with a carboxyl-terminated PEG (Nektar Corp.) in the presence of, for example, EDC or DCC to form the following structure represented by a formula (XXVIII):

(XXVIII)

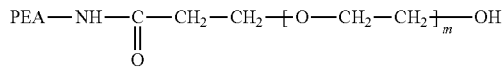

wherein m is an integer not equal to 0.

In another embodiment, either a succinimidyl derivative of mPEG (Nektar Corp.) or an isocyanate-terminated mPEG (Nektar Corp.) can be reacted with an amino-terminated PEA under conditions known to those of skill in the art. In another embodiment, the carboxyl group of a carboxyl-terminated PEA can be activated with, for example, EDC or DCC and combined with an amino-terminated mPEG (Nektar Corp.). In another embodiment, an amino-terminated mPEG can be combined with a high molecular weight PEA in the presence of an acid or base catalyst through amination of ester groups in a high molecular weight PEA. In another embodiment, an amino-terminated PEA can be combined with a methacrylate-terminated mPEG (Nektar Corp.) in the presence of an initiator capable of undergoing thermal or photolytic free radical decomposition. Examples of suitable initiators include benzyl-N,N-diethyldithiocarbamate or p-xylene-N,N-diethyldithiocarbamate. In another embodiment, an amino-terminated PEA can be combined with ethylene oxide in a living polymerization reaction, which is an unterminated anionic polymerization kept alive and controlled by maintaining a pure system. A living polymerization reaction can be killed through addition of a terminating agent such as, for example, water.

The following examples are provided to further illustrate embodiments of the present invention.

Example 1

The PEA of formula (XXIV) can be prepared according to the following procedure:
Method of Preparing of L-Leucine-ε-L-Lysine Benzyl Ester-2TosOH L-leucine-ε-L-lysineHCl (New England Peptide, Inc.) (73.86 gm, 0.25 mole), p-toluenesulfonic acid (152.15 gm, 0.80 mole), benzyl alcohol (100.9 ml, 0.97 mole), and 200 ml of benzene is added to a 1 liter reaction flask equipped with a mechanical stirrer, Dean Stark trap, thermometer and argon inlet. The mixture is heated to 80° C. for 8 hours, and condensate is collected in the Dean Stark trap. The mixture is transferred to a 2 liter flask, and 1 liter of ethyl acetate is added to the mixture with stirring. The mixture is stored overnight at 4° C., and L-Leucine-ε-L-Lysine Benzyl Ester-2TosOH is isolated by filtration.
Method of Preparing co-poly-{[N,N'-sebacoyl-bis-(L-leucine)-1,6-hexylene diester]-[N,N'-sebacoyl-L-leucine-L-lysine mPEG amide]}

Dry triethylamine (61.6 ml, 0.44 mole) is added to a mixture of di-p-toluenesulfonic acid salt of bis-(L-leucine)-1,6-hexylene diester (120.4 gm, 0.18 mole), di-p-toluenesulfonic acid salt of L-leucine-ε-L-lysine benzyl ester (13.863 gm, 0.02 mole), and di-p-nitrophenyl sebacinate (88.88 gm, 0.2 mole) in dry DMAC (110 ml). The mixture is stirred and heated at 80° C. for 12 hours. The mixture is then cooled to room temperature, diluted with ethanol (300 ml), and poured into 1 liter of water. The polymer is separated, washed with water, and vacuum dried. A free carboxyl group is generated by hydrogenolysis over a palladium catalyst. Ethanol (1200 ml) and the polymer (100 mg) is added to a 2 liter flask with a palladium on carbon catalyst (5 gm) (Aldrich). Hydrogen is bubbled and stirred through the mixture for 24 hours, and the palladium on carbon catalyst is separated by centrifugation leaving a solution.

This solution is added to hexane/ethyl acetate (10 liters of a 50/50 mixture) with stirring to precipitate co-poly-{[N,N'-sebacoyl-bis-(L-leucine)-1,6-hexylene diester]-[N,N'-sebacoyl-L-leucine-L-lysine]}. The polymer is filtered, dissolved (50 gm) in THF (1500 ml) in a 2 liter flask with stirring and an argon purge, and then combined with N-hydroxysuccinimide (1.32 gm, 0.0115 mole) and dicyclohexylcarbodiimide (2.37 gm, 0.0115 mole). The combination is stirred for 24 hours at ambient temperature and filtered to remove 1,3-dicyclohexylurea. The filtered solution is combined with an amino-terminated mPEG (MW 5000, 46 gm, 0.0092 moles) (Nektar Corp.) in a 2 liter flask and stirred for 6 hours under argon. The co-poly-{[N,N'-sebacoyl-bis-(L-leucine)-1,6-hexylene diester]-[N,N'-sebacoyl-L-leucine-L-lysine mPEG amide]} is precipitated by slow addition of the solution into hexane/ethyl acetate (50/50) with stirring.

Example 2

The copolymer represented by formula (XIX) can be prepared in a manner analogous to the method used to prepare the copolymer represented by formula (XXIV) by replacing the L-leucine-ε-L-lysine HCl with L-lysine HCl.

Example 3

The PEA of formula (XXII) can be prepared according to the following procedure:
Method of Preparing co-poly-{[N,N'-sebacoyl-bis-(L-leucine)-1,4-butylene diester]-[N,N'-sebacoyl-L-lysine-4-carboxy-TEMPO Anhydride]}

Dry triethylamine (61.6 ml, 0.44 mole) is added to a mixture of a di-p-toluenesulfonic acid salt of bis-(L-leucine)-1,4-butylene diester (118.82 gm, 0.18 mole), a di-p-toluenesulfonic acid salt of L-lysine benzyl ester (11.603 gm, 0.02 mole), and di-p-nitrophenyl sebacinate (88.88 gm, 0.2 mole) in dry DMAC (110 ml). The mixture is stirred and heated at 80° C. for 12 hours, cooled to room temperature, diluted with ethanol (300 ml), and poured into water (1 liter). The polymer is separated, washed with water, and dried under vacuum. A free carboxyl group can be generated by hydrogenolysis over a palladium catalyst. Ethanol (1200 ml) is combined with the polymer (100 g) and a palladium on carbon catalyst in a 2 liter flask. Hydrogen is bubbled and stirred through the solution for 24 hours. The catalyst is separated by centrifugation leaving a solution. This solution is slowly added to hexane/ethyl acetate (10 liters, 50/50) with stirring to precipitate co-poly-{[N,N'-sebacoyl-bis-(L-leucine)-1,6-hexylene diester]-[N,N'-sebacoyl-L-lysine]}. The polymer (50 gm) is filtered, dissolved and stirred in dry 1,1,2-trichloroethane (1600 ml) in a 2 liter flask, and acetic anhydride (2.24 gm, 0.022 mole) and 4-carboxyl-TEMPO (4.01 gm, 0.02 mole) is added to the 2 liter flask. The mixture is distilled under vacuum to remove DMF at 80° C. and a sufficient amount of heat is applied to achieve a distillation rate of about 5 ml/min. The solution is stirred for two hours, cooled to room temperature, and the co-poly-{[N,N'-sebacoyl-bis-(L-leucine)-1,4-butylene diester]-[N,N'-sebacoyl-L-lysine-4-carboxy-TEMPO anhydride]} is precipitated by slow addition of the solution to hexane/ethyl acetate (4 liters, 50/50) with stirring.

Example 4

The PEA of formula (XXV) can be prepared according to the following procedure:
Method of Preparing Conjugate of estradiol and 3,9-diethylidene-2,4,8,10-tetraoxaspiro-[5,5]-undecane (DETOSU)

Dry THF (40 ml) is combined with DETOSU (5 gm, 0.0236 mole) and six drops of 1% p-toluenesulfonic acid in THF in a 100 ml flask. A solution of estradiol (6.42 gm. 0.0236 mole) in THF (20ml) is slowly added with stirring for over an hour. The estradiol-DETOSU conjugate is isolated by rotary evaporation.
Method of Preparing bis-(L-leucine)-1,3-propylene diester-2-one L-leucine (32.80 gm, 0.25 mole), p-toluenesulfonic acid (104.6 gm, 0.55 mole), 1,3-dihydroxy acetone dimer (22.53 gm, 0.125 mole), and 200 ml of benzene are added to a 1 liter flask. The solution is heated at 80° C. for 8 hours, and condensate is collected in a Dean Stark trap. The solids are separated from the solvents by rotary evaporation, rinsed in a Buchner funnel with water (2, 1 liter portions) and dried in a vacuum oven.
Method of Preparing co-poly-{[N,N'-sebacoyl-bis-(L-leucine)-1,4-butylene diester]-[N,N'-sebacoyl-bis-L-leucine-1,3-propylene diester-2-one]}

Dry triethylamine (61.6 ml, 0.44 mole) is added to a mixture of a di-p-toluenesulfonic acid salt of bis-(L-leucine)-1,4-butylene diester (118.82 gm, 0.18 mole), a di-p-toluenesulfonic acid salt of bis-(L-leucine)-1,3-propylene diester-2-one (13.20 gm, 0.02 mole), and di-p-nitrophenyl sebacinate (88.88 gm, 0.2 mole) in dry DMAC (110 ml). The mixture is stirred and heated at 80° C. for 12 hours, cooled to room temperature, diluted with ethanol (300 ml), and poured into water (1 liter). The polymer is separated, washed with water, and dried under a vacuum. The polymer (80.35 gm), dry THF (250 ml), sodium cyanoborohydride (10.49 gm, 0.167 mole), and p-touluenesulfonic acid (6 drops of a 1% solution) in THF is added to a 500 ml flask. The mixture is stirred for two hours at ambient temperature, poured into chloroform (500 ml), and extracted with 3 portions of aqueous sodium bicarbonate (250 ml, 1M portions). Chloroform is removed by rotary evaporation, and the remaining solvent is removed by drying overnight in a vacuum oven at ambient temperature. The polymer (60 gm), dry THF (250 ml), and the estradiol-DETOSU conjugate (6.64 gm, 0.0137 mole) is added to a 500 ml flask and stirred at room temperature for two hours. The polymer is precipitated by slow addition of the solution into hexane/ethyl acetate (2 liters, 50/50) with stirring.

Example 5

Method of Preparing an Amino-Terminated PEA or a Carboxyl-Terminated PEA

The monomers used in a preparation of PEA provide a roughly 50/50 distribution between amino and activated carboxy-terminated chains at any point during the polymerization. Amino-terminated PEAs can be prepared using a biocompatible, low molecular weight chain-stopper, 1,4-diaminobutane (putrescine) that is added in a large excess to terminate all chains with amino groups at the end of the polymerization, or when the polymerization has reached the desired molecular weight. Carboxyl-terminated PEAs can be prepared by several methods. In one method, a dicarboxylic acid compound such as, for example, di-p-nitrophenyl sebacinate, can be combined with the PEA in excess. This embodiment is simple, but it has a potential drawback of lowering the final molecular weight of the polymer. Another method is to further derivatize a PEA containing a 50/50 distribution of amino-terminated and activated-carboxyl-terminated chains by reacting the PEA with a reagent example.g., succinic anhydride, to convert amino groups to carboxyl groups.

Method of Preparing an Amino-Terminated co-poly-{[N,N'-sebacoyl-bis-(L-leucine)-1,6-hexylene diester]-[N,N'-sebacoyl-L-lysine benzyl ester]}

Dry triethylamine (61.6 ml, 0.44 mole) is added to a mixture of a di-p-toluenesulfonic acid salt of bis-(L-leucine)-1,6-hexylene diester (123.86 gm, 0.18 mole), a di-p-toluenesulfonic acid salt of L-lysine benzyl ester (11.603 gm, 0.02 mole), and di-p-nitrophenyl sebacinate (88.88 gm, 0.2 mole) in dry DMAC (110 ml). The mixture is stirred and heated at 80° C. for 4 hours, at which point 1,4-diaminobutane (15 gm, 0.17 mole) is added, and the mixture is stirred at 80° C. for an additional hour. The solution is cooled to room temperature, diluted with ethanol (300 ml), and poured into a phosphate buffer (2 liters, 0.1 M, pH 7). The polymer is collected by filtration, suspended in chloroform (1 liter), and extracted with 3 portions of phosphate buffer (0.1 M, pH 7, 1 liter portions). The chloroform is removed by rotary evaporation, and the amino-terminated co-poly-{[N,N'-sebacoyl-bis-(L-leucine)-1,6-hexylene diester]-[N,N'-sebacoyl-L-lysine benzyl ester]} is dried overnight in a vacuum oven at ambient temperature.

Method of preparing an carboxy-terminated co-poly-{[N,N'-sebacoyl-bis-(L-leucine)-1,6-hexylene diester]-[N,N'-sebacoyl-L-lysine benzyl ester]}

Dry triethylamine (61.6 ml, 0.44 mole) is added to a mixture of a di-p-toluenesulfonic acid salt of bis-(L-leucine)-1,6-hexylene diester (123.86 gm, 0.18 mole), a di-p-toluenesulfonic acid salt of L-lysine benzyl ester (11.603 gm, 0.02 mole), and di-p-nitrophenal sebacinate (88.88 gm, 0.2 mole) in dry DMAC (110 ml). The mixture is stirred and heated at 80° C. for 4 hours, at which point succinic anhydride (17 gm, 0.17 mole) is added and the mixture is stirred at 80° C. for an additional hour. The solution is cooled to room temperature, diluted with ethanol (300 ml), and poured into a phosphate buffer (2 liters, 0.1 M, pH 7). The polymer is collected by filtration, suspended in chloroform (1 liter), and extracted with 3 portions of phosphate buffer (0.1 M, pH 7, 1 liter portions). The chloroform is removed by rotary evaporation, and the carboxy-terminated co-poly-{[N,N'-sebacoyl-bis-(L-leucine)-1,6-hexylene diester]-[N,N'-sebacoyl-L-lysine benzyl ester]} is dried overnight in a vacuum oven at ambient temperature. This preparation can result in a polymer wherein all of the endgroups are carboxyl, and some of the endgroups are still activated with a p-nitrophenol group. This group may be suitable for subsequent coupling steps such as with, for example, an amino-terminated moiety. If it is desired to convert all endgroups to free carboxylic endgroups, the following steps would be inserted into the synthesis: after the addition of the succinic anhydride and stirring for one hour, L-leucine (11.2 gm, 0.085 mole) and triethylamine (8.59 gm, 0.085 mole) would be added and stirred for an additional hour.

Example 6

Method of Preparing a PEA-Heparin Conjugate by Combining Heparin with an Amino-Terminated PEA A PEA-heparin conjugate can be prepared by connecting an amino-terminated PEA with a heparin-aldehyde adduct formed by oxidative cleavage of heparin. An amino-terminated PEA (50 g) is added to a reactor containing DMAC/water (1 liter, 40:1) under nitrogen. A heparin-aldehyde adduct (7.5 g) and cyanoborohydride (0.2 g; 3.2 mmol) is added to the solution and heated to 60° C. for 12 hours under nitrogen, cooled to room temperature, and added dropwise to methanol. The PEA-heparin conjugate is filtered, washed with 3 portions of water (250 mL portions), and dried under vacuum.

Alternate method of preparing a PEA-heparin conjugate by EDC coupling of a D-glucoronic acid or L-iduronic acid functionality of the heparin in a DMAC/water medium Heparin (20 g) is combined with a DMAC/water solution (450 g) and N-(3'-dimethylaminopropyl)-N'-ethylcarbodiimide (0.2 g, 1.0 mmol). The solution is stirred at room temperature for 2 hours under nitrogen, and the PEA-amine (50 g) is added to the DMAC/water solution (40/1; 500 g) and mixed at pH 4.75 for 4 hours. The solution is neutralized with sodium hydroxide (0.1 M) to pH 7.5 and stirred overnight under nitrogen. The PEA-heparin conjugate is precipitated by addition of the solution into THF, filtered and washed with water.

Example 7

Method of Preparing a PEA-PEG Conjugate with an Amino-Terminated PEA

An amino-terminated PEA can be PEGylated by aldehyde coupling/imine reduction, carbodiimide coupling of a carboxyl terminated PEG, and maleimide coupling of a PEG-maleimide to an amine terminated PEA.

An amino-terminated PEA can be conjugated to PEG by aldehyde coupling/imine reduction. A PEA (50 g) is dissolved in anhydrous DMAC (230 g) in the coupling of PEG to amino-terminated PEA. A PEG-butyraldehyde (MW 1000-50,000, 7.5 g) is combined with sodium cyanoborohydride (1.0 g) and stirred overnight at room temperature under nitrogen. The polymer is precipitated by addition of the solution with stirring in methanol, redissolved in DMAC, reprecipitated in water, and dried under vacuum.

An amino-terminated PEA can be conjugated to PEG by carbodiimide coupling of a carboxyl terminated PEG using DCC/NHS coupling. An amino-terminated PEA (50 g) is added to anhydrous THF (116 g; 1-35% w/w). Anhydrous THF (116 g) and carboxyl-terminated PEG (10 kD, 7.0 g, 0.7 mmol), dicyclohexylcarbodiimide (0.15 g; 7.1 mmol) (DCC) is added to a reactor containing N-hydroxysuccinimide (0.10 g/8 mmol) (NHS) to form a mixture. The mixture is stirred under nitrogen for 2 hours at room temperature, and the amino-terminated PEA solution is added to the mixture in a dropwise manner, stirred overnight at room temperature, and added dropwise to methanol to form a PEA-PEG precipitate. The precipitate is filtered and dried under vacuum.

III. Agent as a Physical Blend with the PEA Polymer

A polymer of the present invention can be a physical blend of the active agent with the PEA polymer. The active agent may be completely solubilized in the solvent or solvent(s) used to dissolve the PEA. Additionally, the active agent may be present as a suspension or dispersion of fine particles. A water miscible solvent is used to dissolve the PEA. Consequently, the active agent may also be dissolved, or suspended, in a second, immiscible solvent phase present in the PEA phase.

It is to be appreciated that the disclosed specific embodiments are only meant to be illustrative of the present invention and one of ordinary skill in the art will appreciate the ability to substitute features or to eliminate disclosed features. As such, the scope of the Applicant's invention is to be measured by the appended claims that follow.

The invention claimed is:

1. A composition comprising:
   a first polymer cross-linked with a second polymer, the second polymer being different than the first polymer, wherein the first polymer comprises a poly (ester amide) polymer comprising an amino acid, and the second polymer comprises a biodegradable polymer;
   a therapeutic agent; and
   a solvent, wherein the first polymer cross-linked with the second polymer and the solvent are combined to form a heterogeneous mixture in liquid form and the solvent is at least partially water miscible such that the solvent diffuses out of the heterogeneous mixture in vivo, and wherein the average molecular weight of the first polymer is from 10,000 Daltons to 200,000 Daltons.

2. The composition of claim 1, wherein
   the solvent is selected from the group consisting of ethanol, propylene glycol, benzyl benzoate, benzyl alcohol, n-methylpyrrolidone (NMP) and dimethyl sulfoxide (DMSO).

3. The composition of claim 1 wherein the amino acid is selected from the group consisting of lysine, tyrosine, glutamic acid and cysteine.

4. The composition of claim 1 wherein the amino acid is a first amino acid, the composition further comprising a second amino acid, wherein at least one of the first amino acid or the second amino acid is lysine.

5. The composition of claim 4 wherein both the first amino acid and the second amino acid are lysine.

6. The composition of claim 1 wherein the amino acid is a first amino acid, the composition further comprising a second amino acid, wherein at least one of the first amino acid or the second amino acid is selected from the group consisting of glycine, valine, alanine, leucine, isoleucine, phenylalanine.

7. The composition of claim 1 wherein the second polymer is one of poly(butyl methacrylate), poly(ethyl methacrylate), poly(ethyl methacrylate-co-butyl methacrylate), poly(vinylidene fluoride), poly(vinylidene fluoride-co-hexafluoro propene), poly(N-vinyl pyrrolidone), poly(hydroxyvalerate), poly(L-lactic acid), polycaprolactone, poly (lactide-co-glycolide), poly(hydroxybutyrate), poly (hydroxybutyrate-co-valerate), polydioxanone, polyorthoester, polyanhydride, poly(glycolic acid), poly(D,L-lactic acid), poly(glycolic acid-co-trimethylene carbonate), polyphosphoester, polyphosphoester urethane, poly (amino acid), cyanoacrylate, poly(trimethylene carbonate), poly(iminocarbonate), co-poly (ether-ester), polyalkylene oxalate, and polyphosphazene.

8. The composition of claim 1 wherein the second polymer is a biomolecule selected from one of fibrin, fibrinogen, cellulose, starch, collagen and hyaluronic acid.

9. The composition of claim 1 wherein the second polymer is one of polyurethane, silicone, polyester, polyolefin, polyisobutylene, ethylene-alphaolefin copolymer, polyvinyl chloride, polyvinyl methyl ether, polyvinylidene chloride, polyacrylonitrile, polyvinyl ketones, polystyrene, polyvinyl acetate, poly(ethylene-co-vinyl alcohol) (EVAL), ethylene-methyl methacrylate copolymer, acrylonitrile-styrene copolymer, ABS resin, ethylene-vinyl acetate copolymer, Nylon 66, polycaprolactam, alkyd resin, polycarbonate, polyoxymethylene, polyimide, polyether, epoxy resin, rayon, rayon-triacetate, cellulose, cellulose acetate, cellulose butyrate, cellulose acetate butyrate, cellophane, cellulose nitrate, cellulose propionate, cellulose ether, and carboxymethyl cellulose.

10. A composition comprising:
    a first polymer cross-linked with a second polymer, wherein the first polymer is a poly (ester amide) polymer comprising the reaction product of a diacid, a diol, a triol, a first diol, and a second diol or diamine, and the second polymer is a biodegradable polymer;
    a therapeutic agent; and
    a solvent, wherein the first polymer cross-linked with the second polymer and the solvent are combined to form a heterogeneous mixture in liquid form and the solvent is at least partially water miscible such that the solvent diffuses out of the heterogeneous mixture in vivo.

11. The composition of claim 10 wherein the diacid of the poly (ester amide) polymer has between two and twelve carbons and comprises one of an aliphatic diacid and an unsaturated diacid.

12. The composition of claim 10 wherein the diol of the poly (ester amide) polymer comprises between two and twelve carbons and comprises one of a branched diol and an unsaturated diol.

13. The composition of claim 10 wherein the second diol or diamine is within a backbone of the poly (ester amide) polymer.

14. A composition comprising:
a first polymer cross-linked with a second polymer, wherein the first polymer is a poly (ester amide) polymer comprising the reaction product of an amino acid, a diamine and a hydroxyacid, and the second polymer is a biodegradable polymer;
a therapeutic agent; and
a solvent, wherein the first polymer cross-linked with the second polymer and the solvent are combined to form a heterogeneous mixture in liquid form and the solvent is at least partially water miscible such that the solvent diffuses out of the heterogeneous mixture in vivo.

15. The composition of claim 14 wherein the diamine is one of putrescine or cadaverene.

16. The composition of claim 1, wherein the therapeutic agent is connected to the poly (ester amide) polymer as a pendant group or an in-chain group.

17. The composition of claim 1, wherein the therapeutic agent is a polymeric agent.

18. The composition of claim 1 wherein the therapeutic agent has a low molecular weight in the approximate range of 100 grams per mole to 200,000 grams per mole.

19. The composition of claim 1 wherein the therapeutic agent is at least one of a pharmaceutical agent, a biologic, or an image-enhancing agent.

20. The composition of claim 19 wherein the biologic is one of a cell, a protein, a peptide, a monoclonal antibody, an amino acid, or a polyoligonucleotide.

21. The composition of claim 19 wherein the pharmaceutical agent is one of an anti-inflammatory, an anti-platelet, an anti-coagulant, an anti-fibrin, an anti-thrombotic, an anti-mitotic, an anti-biotic, an anti-allergic, an anti-oxidant, an anti-proliferative, or an anti-migratory.

22. The composition of claim 19 wherein the image-enhancing agent is one of a radiopaque dye or a magnetic resonance imaging agent.

23. The composition of claim 19 wherein the pharmaceutical agent comprises Sirolimus, Everolimus, ABT-578, or Paclitaxel.

24. The composition of claim 1 wherein the therapeutic agent is one of actinomycin D, actinomycin IV, actinomycin I1, actinomycin X1, actinomycin C1, dactinomycin, paclitaxel, docetaxel, methotrexate, azathioprine, vincristine, vinblastine, fluorouracil, doxorubicin hydrochloride mitomycin, sodium heparin, low molecular weight heparins, heparinoids, hirudin, argatroban, forskolin, vapiprost, prostacyclin, prostacyclin analogues, dextran, D-phe-pro-arg-chloromethylketone, dipyridamole, glycoprotein IIb/IIIa platelet membrane receptor antagonist antibody, recombinant hirudin, thrombin inhibitors, angiopeptin, angiotensin converting enzyme inhibitors, cilazapril, lisinopril, nifedipine, colchicines, fibroblast growth factor antagonists, fish oil, omega 3-fatty acid, histamine antagonists, lovastatin, antibodies specific for Platelet-Derived Growth Factor (PDGF) receptors, nitroprusside, phosphodiesterase inhibitors, prostaglandin inhibitors, suramin, serotonin blockers, steroids, thioprotease inhibitors, triazolopyrimidine, nitric oxide, pemirolast potassium, free radical scavengers, nitric oxide donors, rapamycin, tacrolimus; 40-O-(2hydroxy)ethyl-rapamycin; 40-O-(3-hydroxy)propyl-rapamycin; 40-O-[2-(2-hydroxy)ethoxy]ethyl-rapamycin; tetrazole containing rapamycin analogs, estradiol, clobetasol, idoxifen, tazarotene, alpha-interferon, epithelial cells, genetically engineered epithelial cells, dexamethasone, free radical 2,2',6,6'-tetramethyl-1-piperinyloxy, free radical 4-amino-2,2',6,6'-tetramethyl-1-piperinyloxy, free radical, free radical 4-hydroxy-2,2',6,6'-tetramethyl-piperidene-1-oxy, free radical 2,2',3,4,5,5'-hexamethyl-3-imidazolinium-1-yloxy methyl sulfate, free radical 16-doxyl-stearic acid, superoxide dismutase mimic, S-nitrosothiols, nitrites, N-oxo-N-nitrosamines, substrates of nitric oxide synthase, diazenium diolates, spermine diazenium diolate, acetriozate, diatriozate, iodimide, ioglicate, iothalamate, ioxithalamate, selectan, uroselectan, diodone, metrizoate, metrizamide, iohexol, ioxaglate, iodixanol, lipidial, ethiodol, gadodiamide, gadopentetate, gadoteridol and gadoversetamide and a prodrug, metabolite, analog, homologue, congener, derivative, salt or combination thereof.

25. The composition of claim 1 wherein the therapeutic agent is a triene macrolide antibiotic or a taxane anti-proliferative.

26. A composition comprising:
a first polymer cross-linked with a second polymer, the second polymer being different than the first polymer, wherein the first polymer comprises a poly (ester amide) polymer comprising an amino acid, and the second polymer comprises a biodegradable polymer;
a therapeutic agent; and
a solvent, wherein the first polymer cross-linked with the second polymer and the solvent are combined to form a heterogeneous mixture in liquid form and the solvent is at least partially water miscible such that the solvent diffuses out of the heterogeneous mixture in vivo,
wherein the poly (ester amide) polymer comprises the reaction product of a diacid, a first diol, and a second diol, and the first diol or the second diol comprises between two and twelve carbons and comprises one of a branched diol and an unsaturated diol, and wherein the average molecular weight of the first polymer is from 10,000 Daltons to 200,000 Daltons.

* * * * *